United States Patent [19]
Wheeler et al.

[11] Patent Number: 5,981,501
[45] Date of Patent: Nov. 9, 1999

[54] METHODS FOR ENCAPSULATING PLASMIDS IN LIPID BILAYERS

[75] Inventors: Jeffery J. Wheeler, Richmond; Michael Hope; Pieter R. Cullis, both of Vancouver; Marcel B. Bally, Bowen Island, all of Canada

[73] Assignee: Inex Pharmaceuticals Corp., Vancouver, B.C., Canada

[21] Appl. No.: 08/484,282

[22] Filed: Jun. 7, 1995

[51] Int. Cl.$^6$ .............................. A61K 48/00; A61K 9/127
[52] U.S. Cl. .............................. 514/44; 264/4.3; 264/4.6; 424/450; 436/829; 514/55; 514/851
[58] Field of Search ................... 264/4.3, 4.6; 424/450; 436/829; 935/54, 56, 55; 514/44, 851

[56] References Cited

U.S. PATENT DOCUMENTS

| | | | |
|---|---|---|---|
| 4,394,448 | 7/1983 | Szoka, Jr. et al. | 424/450 X |
| 4,438,052 | 3/1984 | Weder et al. | 264/4.6 |
| 4,515,736 | 5/1985 | Deamer | 264/4.3 |
| 4,598,051 | 7/1986 | Papahadjopoulos et al. | 436/829 X |
| 4,897,355 | 1/1990 | Eppstein et al. | 435/240.2 |
| 5,171,678 | 12/1992 | Behr et al. | 435/172.3 |
| 5,208,036 | 5/1993 | Eppstein et al. | 424/450 |
| 5,264,618 | 11/1993 | Felgner et al. | 560/224 |
| 5,279,833 | 1/1994 | Rose | 424/450 |
| 5,283,185 | 2/1994 | Epand et al. | 435/172.3 |
| 5,320,906 | 6/1994 | Eley et al. | 428/402.2 |
| 5,545,412 | 8/1996 | Eppstein et al. | 424/450 |

FOREIGN PATENT DOCUMENTS

| | | |
|---|---|---|
| WO 91/16024 | 10/1991 | WIPO .............................. A61F 13/00 |
| WO 93/05162 | 3/1993 | WIPO .............................. C12N 15/63 |
| WO 93 12756 | 7/1993 | WIPO . |
| WO 95 02698 | 1/1995 | WIPO . |
| WO 96 10390 | 4/1996 | WIPO . |

OTHER PUBLICATIONS

M. Barinaga: "Gene Therapy—Step Taken Toward Improved Vectors for Gene Transfer", *Science*, vol. 266, Nov. 1994, p. 1326.

E. Marshall: "Gene Therapy's Growing Pains", *Science*, vol. 269, Aug. 1995, pp. 1050–1055.

R. Crystal: "Transfer of Genes to Humans: Early Lessons and Obstacles to Success", *Science*, vol. 270, 1995, pp. 404–410.

S. H. Orkin et al: Report and Recommendations of the Panel to Assess the NIH Investment in Research on Gene Therapy, NIH Report, Dec. 1995.

Hawley–Nelson, et al. Focus 15(3):73 (1993) Lipofectamine™Reagent: A New, Higher Efficiency Polycationic Liposome Transfection Reagent.

Stamatatos, et al., Biochemistry 27:3917–3925 (1988), Interactions of Cationic Lipid Vesicles with Negatively Charged Phospholipid Vesicles and Biological Membranes.

Leventis, et al., Biochem. Biophys. Acta 1023:124 (1990), Interactions of Mammalian Cells with Lipid Dispersions Containing Novel Metabolizable Cationic Amphiphiles.

Ballas, et al., Biochim. Biophys. Acta 939:8–18 (1988).

Duzgunes, Subcellular Biochemistry 11:195–286 (1985).

Szoka et al., Ann. Rev. Biophys. Bioeng. 9:467–508 (1980).

Legendre, Pharm. Res. 9:1235–1242 (1992).

Gao, et al., Biochem. Biophys. Res. Comm. 179:280–285 (1991).

Woodle, et al., Biochim. Biophys. Acta 1105:193–200 (1992), Versatility in Lipid Compositions Showning Prolonged Circulation with Sterically Stabilized Liposomes.

Juliano, Biochem. Biophys. Res. Commun. 63:651–658 (1975).

Zhu, et al., Science 261:209–211 (1993), Systemic Gene Expression After Intravenous DNA Delivery Into Adult Mice.

Hyde et al., Nature 362:250–256 (1993), Correction of the Ion Transport Defect in Systic Fibrosis Transgenic Mice by Gene Therapy.

Brigham, et al., Am. J. Med. Sci. 298:278–281 (1989), Rapid Communication: In Vivo Transfection of Murine Lungs with a Fuctioning Prokaryotic Gene Using a Liposome Vehicle.

Puyal et al., Eur. J. Biochem. 228:697–703 (1995).

*Primary Examiner*—Richard D. Lovering
*Attorney, Agent, or Firm*—Townsend and Townsend and Crew

[57] ABSTRACT

Plasmid-lipid particles which are useful for transfection of cells in vitro or in vivo are described. The particles can be formed using either detergent dialysis methods or methods which utilize organic solvents. The particles are typically 65–85 nm, fully encapsulate the plasmid and are serum-stable.

29 Claims, 18 Drawing Sheets

METHODS FOR ENCAPSULATING PLASMIDS IN LIPID BILAYERS

FIELD OF THE INVENTION

This invention relates to formulations for therapeutic nucleic acid delivery and methods for their preparation, and in particular to lipid encapsulated plasmids or antisense constructs. The invention provides a circulation-stable, characterizable delivery vehicle for the introduction of plasmids or antisense compounds into cells. These vehicles are safe, stable, and practical for clinical use.

BACKGROUND OF THE INVENTION

Gene therapy is an area of current interest which involves the introduction of genetic material into a cell to facilitate expression of a deficient protein. There are currently five major methods by which this is accomplished, namely: (i) calcium phosphate precipitation, (ii) DEAE-dextran complexes, (iii) electroporation, (iv) cationic lipid complexes and (v) reconstituted viruses or virosomes (see Chang, et al., *Focus* 10:88 (1988)). Cationic lipid complexes are presently the most effective generally used means of effecting transfection.

A number of different formulations incorporating cationic lipids are commercially available, namely (i) LIPOFECT® (which uses 1,2-dioleyloxy-3-(N,N,N-trimethylamino) propane chloride, or DOTMA, see Eppstein, et al., U.S. Pat. No. 4,897,355); LIPOFECTAMINE® (which uses DOSPA, see Hawley-Nelson, et al., *Focus* 15(3):73 (1993)); and LIPOFECTACE® (which uses N,N-distearyl-N,N-dimethyl-ammonium bromide, or DDAB, see Rose, U.S. Pat. No. 5,279,833). Others have reported alternative cationic lipids that work in essentially the same manner but with different efficiencies, for example 1,2-dioleoyloxy-3-(N,N,N-trimethylamino)propane chloride, or DOTAP, see Stomatatos, et al., *Biochemistry* 27:3917–3925 (1988)); glycerol based lipids (see Leventis, et al., *Biochem. Biophys. Acta* 1023:124 (1990); lipopolyamines (see, Behr, et al., U.S. Pat. No. 5,171,678) and cholesterol based lipids (see Epand, et al., WO 93/105162, and U.S. Pat. No. 5,283,185).

Others have noted that DOTMA and related compounds are significantly more active in transfection assays than their saturated analogues (see, Felgner, et al., W091/16024). However, both DOTMA and DOSPA based formulations, despite being the most efficient of the cationic lipids in effecting transfection, are prohibitively expensive. DDAB on the other hand is inexpensive and readily available from chemical suppliers but is less effective than DOTMA in most cell lines. Another disadvantage of the current lipid systems is that they are not appropriate for intravenous injection.

An examination of the relationship between the chemical structure of the carrier vehicle and its efficiency of transfection has indicated that the characteristics which provide for effective transfection would make a carrier unstable in circulation (see, Ballas, et al., *Biochim. Biophys. Acta* 939:8–18 (1988)). Additionally, degradation either outside or inside the target cell remains a problem (see, Duzghines, *Subcellular Biochemistry* 11:195–286 (1985)). Others who have attempted to encapsulate DNA (Szoka et al., *Ann. Rev. Biophys. Bioeng.* 9:467 (1980); and Deamer, U.S. Pat. No. 4,515,736) made no efforts to ensure a safe, injectable formulation, or arrived at inefficient loading (Legendre, *Pharm. Res.* 9:1235–1242 (1992)).

Ideally, a delivery vehicle for a nucleic acid or plasmid will have the following characteristics: a) small enough and long lived enough to distribute from local injection sites when given intravenously, b) capable of carrying a large amount of DNA per particle to enable transfection of all sizes of genes and reduce the volume of injection, c) homogenous, d) reproducible, e) protective of DNA from extracellular degradation and f) capable of transfecting target cells in such a way that the DNA is not digested intracellularly.

The present invention provides such compositions and methods for their preparation and use.

SUMMARY OF THE INVENTION

In one aspect, the present invention provides methods for the preparation of serum-stable plasmid-lipid particles. In one group of these methods, a plasmid is combined with cationic lipids in a detergent solution to provide a coated plasmid-lipid complex. The complex is then contacted with non-cationic lipids to provide a solution of detergent, a plasmid-lipid complex and non-cationic lipids, and the detergent is then removed to provide a solution of serum-stable plasmid-lipid particles, in which the plasmid is encapsulated in a lipid bilayer. The particles, thus formed, have a size of about 50–150 nm.

In a related group of methods the serum-stable plasmid-lipid particles are formed by preparing a mixture of cationic lipids and non-cationic lipids in an organic solvent; contacting an aqueous solution of plasmid with the mixture of cationic and non-cationic lipids to provide a clear single phase; and removing the organic solvent to provide a suspension of plasmid-lipid particles, in which the plasmid is encapsulated in a lipid bilayer, and the particles are stable in serum and have a size of about 50–150 nm.

In another aspect, the present invention provides plasmid-lipid particles prepared by the above methods.

In yet another aspect, the present invention provides methods of transfecting cells using these plasmid-lipid particles.

DETAILED DESCRIPTION OF THE INVENTION

CONTENTS

Figure 1:
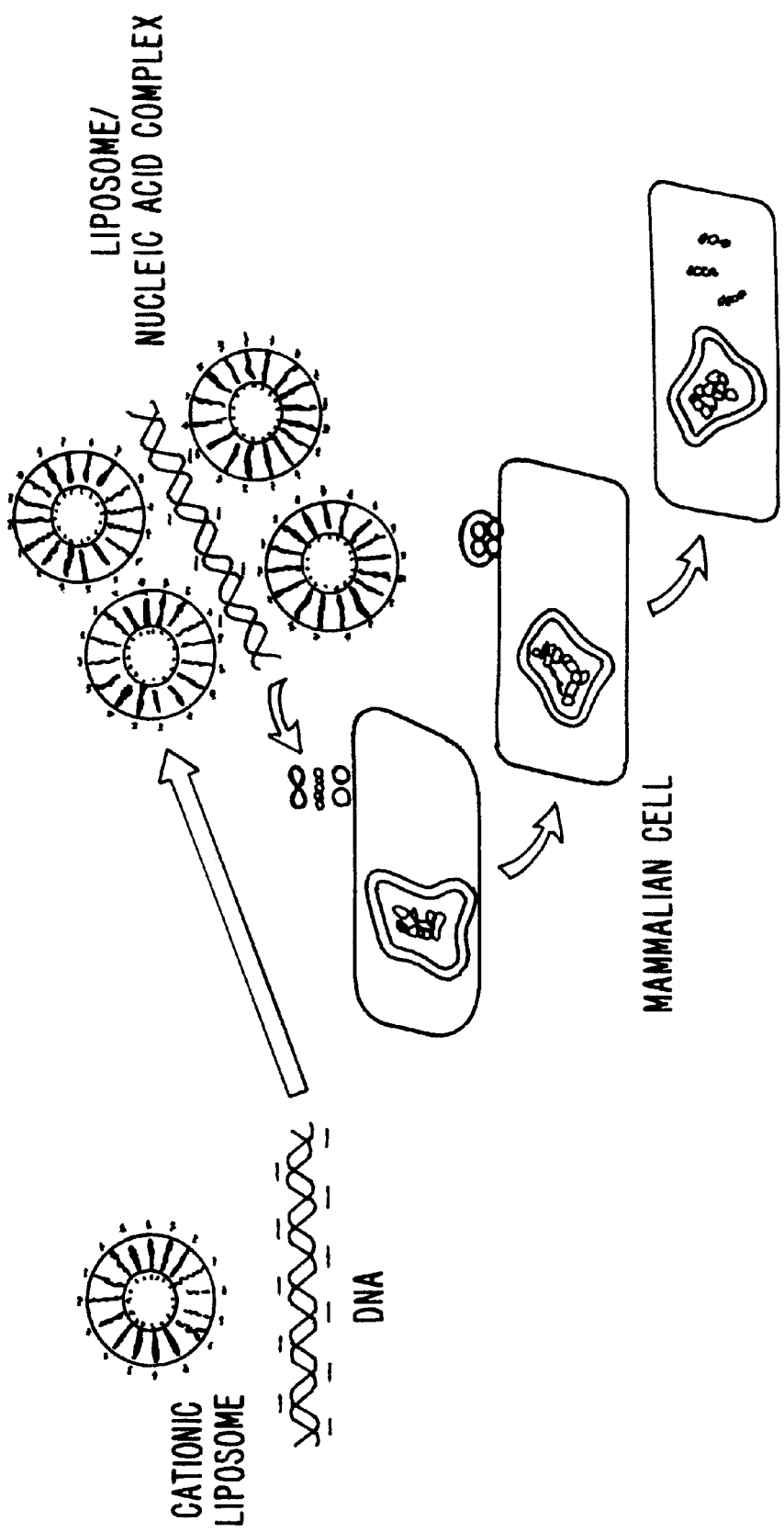
FIG. 1 illustrates a liposome-mediated transfection using "sandwich-type" complexes of DNA.

I. Glossary
II. General
III. Methods of Forming Plasmid-Lipid Particles
IV. Pharmaceutical Preparations
V. Administration of Plasmid-Lipid Particle Formulations
VI. Examples
VII. Conclusion

Glossary

The following abbreviations are used herein: DC-Chol, 3β-(N-(N', N'-dimethylaminoethane)carbamoyl)cholesterol (see, Gao, et al., Biochem. Biophys. Res. Comm. 179:280–285 (1991)); DDAB, N,N-distearyl-N,N-dimethylammonium bromide; DMRIE, N-(1,2-dimyristyloxyprop-3-yl)-N,N-dimethyl-N-hydroxyethyl ammonium bromide; DODAC, N,N-dioleyl-N,N-dimethylammonium chloride (see commonly owned patent application U.S. Ser. No. 08/316,399, now abandoned incorporated herein by reference); DOGS, diheptadecylamidoglycyl spermidine; DOPE, 1,2-sn-dioleylphatidylethanolamine DOSPA, N-(1-(2,3-dioleyloxy)propyl)-N-(2-(sperminecarboxamido)ethyl)-N, N-dimethylammonium trifluoroacetate; DOTAP, N-(1-(2,3-dioleoyloxy)propyl)-N,N,N-trimethylammoniumchloride; DOTMA, N-(1-(2,3-dioleyloxy)propyl)-N,N,N-trimethylammoniumchloride; EPC, egg phosphatidylcholine; RT, room temperature; HEPES, 4-(2-hydroxyethyl)-1-piperazineethanesulfonic acid; HBS, HEPES buffered saline (150 mM NaCl and 20 mM HEPES); PEG-Cer-$C_{20}$, 1-0-(2-(ω-methoxypolyethyleneglycol)succinoyl)-2-N-arachidoyl-sphingosine; PEG-Cer-$C_{14}$, 1-0-(2'-(co-methoxypolyethyleneglycol)succinoyl)-2-N-myristoyl-sphingosine; PBS, phosphate-buffered saline; EGTA, ethylenebis(oxyethylenenitrilo)-tetraacetic acid; OGP, n-octyl β-D-glycopyranoside (Sigma Chemical Co., St. Louis, Mo.); POPC, palmitoyl oleoyl phosphatidylcholine (Northern Lipids, Vancouver, BC); QELS, quasielastic light scattering; TBE, 89 mM Tris-borate with 2 mM EDTA; and EDTA, Ethylenediaminetetraacetic acid (Fisher Scientific, Fair Lawn, N.J.);

The term "acyl" refers to a radical produced from an organic acid by removal of the hydroxyl group. Examples of acyl radicals include acetyl, pentanoyl, palmitoyl, stearoyl, myristoyl, caproyl and oleoyl.

The term "lipid" refers to any fatty acid derivative which is capable of forming a bilayer such that a hydrophobic portion of the lipid material orients toward the bilayer while a hydrophilic portion orients toward the aqueous phase. Hydrophilic characteristics derive from the presence of phosphato, carboxylic, sulfato, amino, sulfhydryl, nitro, and other like groups. Hydrophobicity could be conferred by the inclusion of groups that include, but are not limited to, long chain saturated and unsaturated aliphatic hydrocarbon groups and such groups substituted by one or more aromatic, cycloaliphatic or heterocyclic group(s). Preferred lipids are phosphoglycerides and sphingolipids, representative examples of which include phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine or dilinoleoylphosphatidylcholine could be used. Other compounds lacking in phosphorus, such as sphingolipid and glycosphingolipid families are also within the group designated as lipid. Additionally, the amphipathic lipids described above may be mixed with other lipids including triglycerides and sterols.

The term "non-cationic lipid" refers to any of a number of lipid species which exist either in an uncharged form, a neutral zwitterionic form, or an anionic form at physiological pH. Such lipids include, for example diacylphosphatidylcholine, diacylphosphatidylethanolamine, ceramide, sphingomyelin, cephalin, cardiolipin, and cerebrosides.

The term "cationic lipid" refers to any of a number of lipid species which carry a net positive charge at physiological pH. Such lipids include, but are not limited to, DODAC, DOTMA, DDAB, DOTAP, DC-Chol and DMRIE. Additionally, a number of commercial preparations of cationic lipids are available which can be used in the present invention. These include, for example, LIPOFECTIN® (commercially available cationic liposomes comprising DOTMA and DOPE, from GIBCO/BRL, Grand Island, N.Y., USA); LIPOFECTAMINE® (commercially available cationic liposomes comprising DOSPA and DOPE, from GIBCO/BRL); and TRANSFECTAM® (commercially available cationic liposomes comprising DOGS from Promega Corp., Madison, Wis., USA).

The terms "transfection" and "transformation" are used herein interchangeably, and refer to the introduction of polyanionic materials, particularly nucleic acids, into cells. The term "lipofection" refers to the introduction of such materials using liposome or lipid-based complexes. The polyanionic materials can be in the form of DNA or RNA which is linked to expression vectors to facilitate gene expression after entry into the cell. Thus the polyanionic material used in the present invention is meant to include DNA having coding sequences for structural proteins, receptors and hormones, as well as transcriptional and translational regulatory elements (i.e., promoters, enhancers, terminators and signal sequences) and vectors. Methods of incorporating particular nucleic acids into expression vectors are well known to those of skill in the art, but are described in detail in, for example, Sambrook et al., *Molecular Cloning: A Laboratory Manual* (2nd ed.), Vols. 1–3, Cold Spring Harbor Laboratory, (1989) or *Current Protocols in Molecular Biology,* F. Ausubel et al., ed. Greene Publishing and Wiley-Interscience, New York (1987), both of which are incorporated herein by reference.

"Expression vectors", "cloning vectors", or "vectors" are often plasmids or other nucleic acid molecules that are able to replicate in a chosen host cell. Expression vectors may replicate autonomously, or they may replicate by being inserted into the genome of the host cell, by methods well known in the art. Vectors that replicate autonomously will have an origin of replication or autonomous replicating sequence (ARS) that is functional in the chosen host cell(s). Often, it is desirable for a vector to be usable in more than one host cell, e.g., in *E. coli* for cloning and construction, and in a mammalian cell for expression.

II. General

Figure 2:
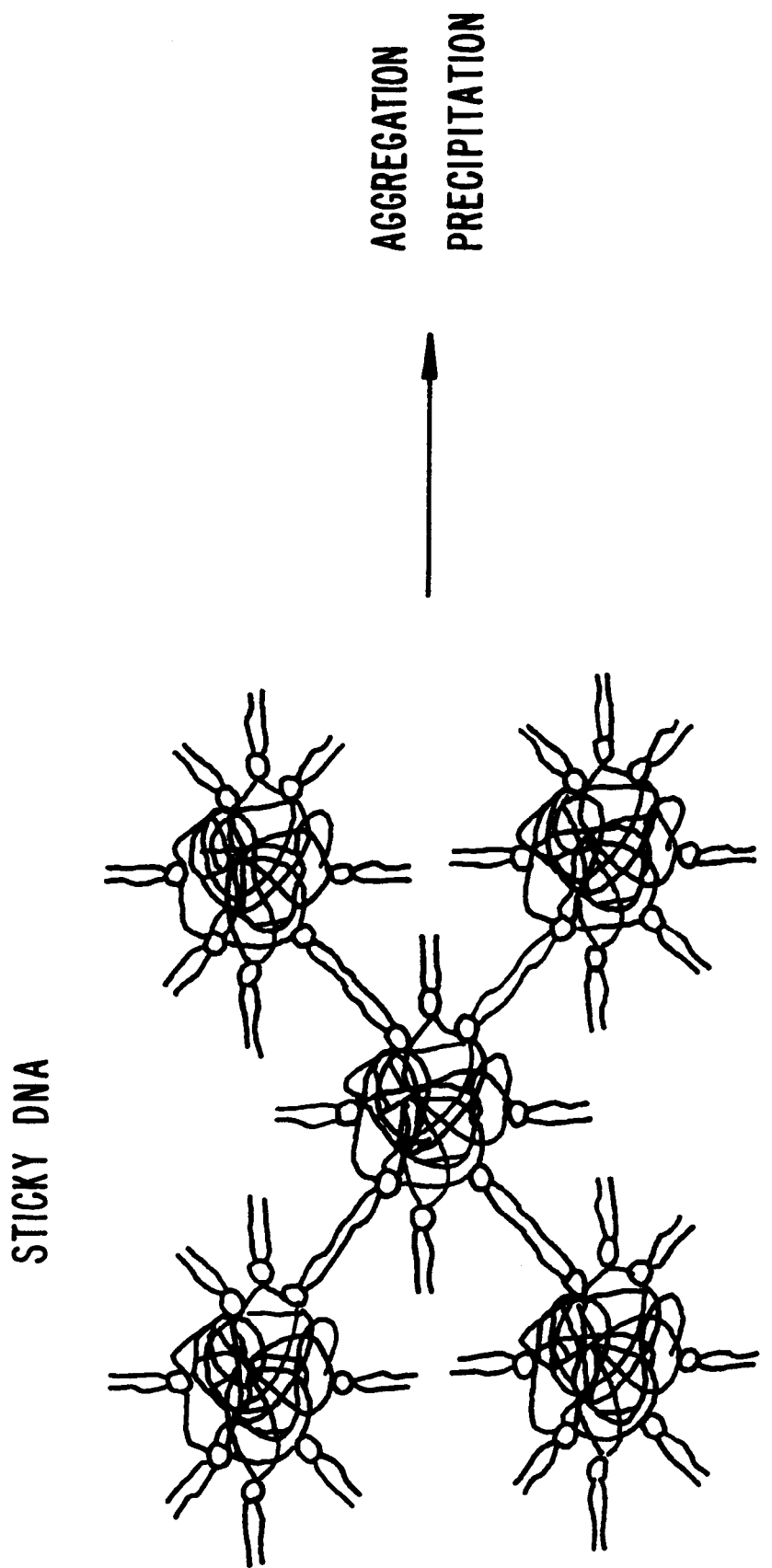
FIG. 2 illustrates an aggregation and precipitation which commonly occurs during the entrapment of large nucleic acids in lipid complexes.
Figure 3:
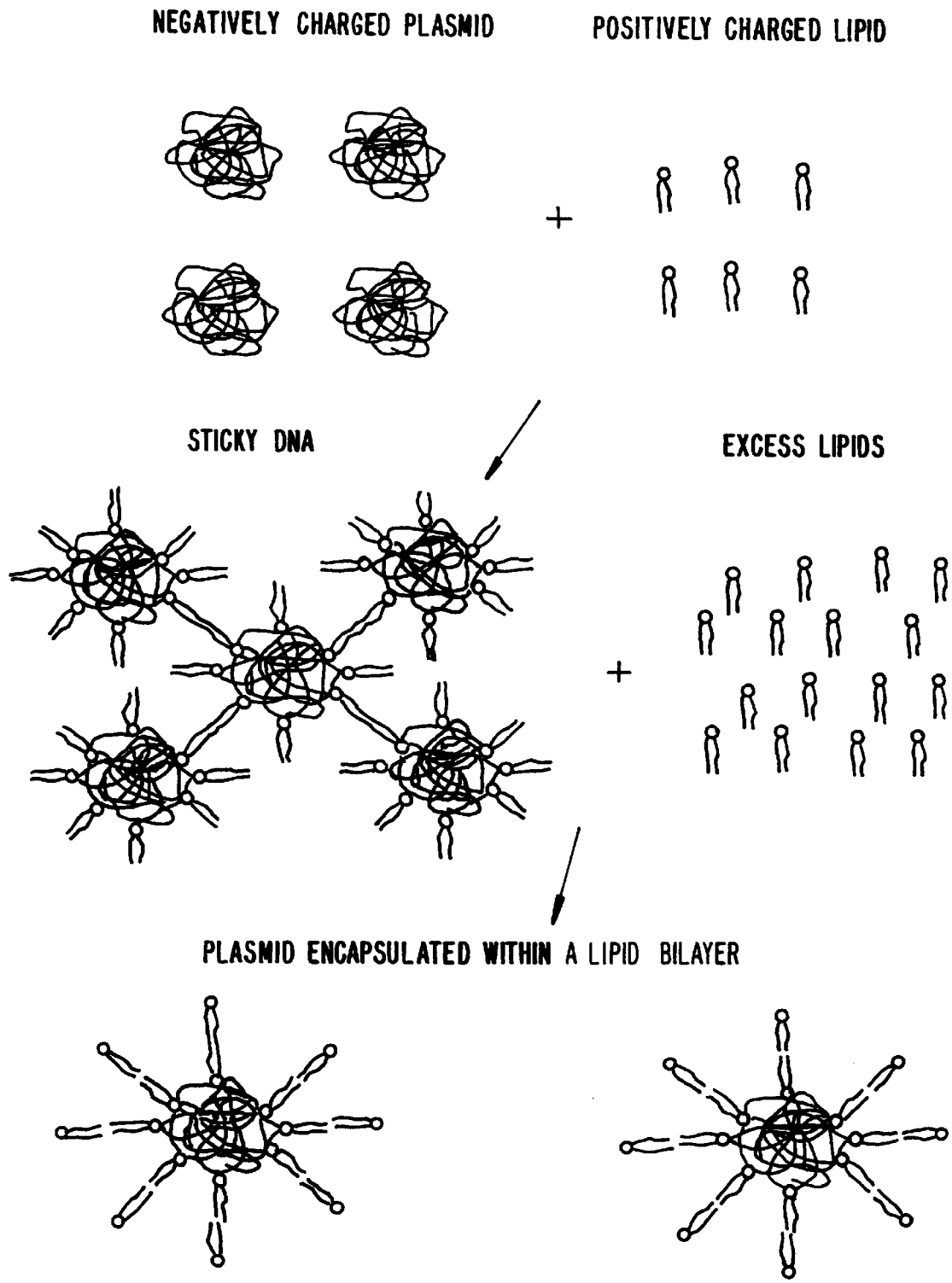
FIG. 3 provides a schematic representation of the preparation of plasmid-lipid particles using the methods of the present invention.

Although directed to the transfer of nucleic acids, and in particular to the transfer of plasmids to cells, the particles of the present invention can be used for delivering essentially any polyanionic molecule. As noted in the Background of the Invention, typical lipid-nucleic acid formulations are formed by combining the nucleic acid with a preformed cationic liposome (see, U.S. Pat. Nos. 4,897,355, 5,264,618, 5,279,833 and 5,283,185. In such methods, the nucleic acid is attracted to the cationic surface charge of the liposome and the resulting complexes are thought to be of the "sandwich-type" depicted in FIG. 1. As a result, a portion of the nucleic acid or plasmid remains exposed in serum and can be degraded by enzymes such as DNAse I. Others have attempted to incorporate the nucleic acid or plasmid into the interior of a liposome during formation. These methods typically result in the aggregation in solution of the cationic lipid-nucleic acid complexes (see FIG. 2). Passive loading of a plasmid into a preformed liposome has also not proven successful. Finally, the liposome-plasmid complexes which have been formed are typically 200 to 400 nm in size and are therefore cleared more rapidly from circulation than smaller sized complexes or particles. The present invention provides a method of preparing serum-stable plasmid-lipid particles in which the plasmid is encapsulated in a lipid-bilayer and is protected from degradation. Additionally, the particles formed have a size of about 50 to about 150 nm, with a majority of the particles being about 65 to 85 nm. The particles can be formed by either a detergent dialysis method or by a modification of a reverse-phase method which utilizes organic solvents to provide a single phase during mixing of the components. Without intending to be bound by any particular mechanism of formation, FIG. 3 depicts a detergent dialysis approach to the formation of the plasmid-lipid particles. With reference to FIG. 3, a plasmid or other large nucleic acid is contacted with a detergent solution of cationic lipids to form a coated plasmid complex. These coated plasmids can aggregate and precipitate. However, the presence of a detergent reduces this aggregation and allows the coated plasmids to react with excess lipids (typically, non-cationic lipids) to form particles in which the plasmid is encapsulated in a lipid bilayer. As noted above, these particles differ from the more classical liposomes both in size (liposomes being typically 200–400 nm) in that there is little or no aqueous medium encapsulated by the particle's lipid bilayer. The methods described below for the formation of plasmid-lipid particles using organic solvents follow a similar scheme.

III. Methods of Forming Plasmid-Lipid Particles

The present invention provides methods for the formation of serum-stable plasmid-lipid particles. While the invention is described with reference to the use of plasmids, one of skill in the art will understand that the methods described herein are equally applicable to other larger nucleic acids or oligonucleotides. In one group of embodiments, the particles are formed using detergent dialysis. Thus, the present invention provides a method for the preparation of serum-stable plasmid-lipid particles, comprising:

(a) combining a plasmid with cationic lipids in a detergent solution to form a coated plasmid-lipid complex;

(b) contacting non-cationic lipids with the coated plasmid-lipid complex to form a detergent solution comprising a plasmid-lipid complex and non-cationic lipids; and (c) dialyzing the detergent solution of step (b) to provide a solution of serum-stable plasmid-lipid particles, wherein the plasmid is encapsulated in a lipid bilayer and the particles are serum-stable and have a size of from about 50 to about 150 nm.

The plasmids which are useful in the present invention are typically nucleotide polymers which are to be administered to a subject for the purpose of repairing or enhancing the expression of a cellular protein. Accordingly, the nucleotide polymers can be polymers of nucleic acids including genomic DNA, cDNA, or mRNA. Still further, the plasmids may encode promoter regions, operator regions, structural regions. When nucleic acids other than plasmids are used the nucleic acids can contain nucleic acid analogs, for example, the antisense derivatives described in a review by Stein, et al., *Science* 261:1004–1011 (1993) and in U.S. Pat. Nos. 5,264,423 and 5,276,019, the disclosures of which are incorporated herein by reference.

The plasmids, or nucleic acids can be single-stranded DNA or RNA, or double-stranded DNA or DNA-RNA hybrid. Examples of double-stranded DNA include structural genes, genes including operator control and termination regions, and self-replicating systems such as plasmid DNA.

Single-stranded nucleic acids include antisense oligonucleotides (complementary to DNA and RNA), ribozymes and triplex-forming oligonucleotides. In order to have prolonged activity, the single-stranded nucleic acids will preferably have some or all of the nucleotide linkages substituted with stable, non-phosphodiester linkages, including, for example, phosphorothioate, phosphorodithioate, phophoroselenate, or O-alkyl phosphotriester linkages.

The nucleic acids used in the present invention will also include those nucleic acids in which modifications have been made in one or more sugar moieties and/or in one or more of the pyrimidine or purine bases. Examples of sugar modifications include replacement of one or more hydroxyl groups with halogens, alkyl groups, amines, azido groups or functionalized as ethers or esters. Additionally, the entire sugar may be replaced with sterically and electronically similar structures, including aza-sugars and carbocyclic sugar analogs. Modifications in the purine or pyrimidine base moiety include, for example, alkylated purines and pyrimidines, acylated purines or pyrimidines, or other heterocyclic substitutes known to those of skill in the art.

Multiple genetic sequences can be also be used in the present methods. Thus, the sequences for different proteins may be located on one strand or plasmid. Promoter, enhancer, stress or chemically-regulated promoters, antibiotic-sensitive or nutrient-sensitive regions, as well as therapeutic protein encoding sequences, may be included as required. Non-encoding sequences may be also be present, to the extent they are necessary to achieve appropriate expression.

The nucleic acids used in the present method can be isolated from natural sources, obtained from such sources as ATCC or GenBank libraries or prepared by synthetic methods. Synthetic nucleic acids can be prepared by a variety of solution or solid phase methods. Generally, solid phase synthesis is preferred. Detailed descriptions of the procedures for solid phase synthesis of nucleic acids by phosphite-triester, phosphotriester, and H-phosphonate chemistries are widely available. See, for example, Itakura, U.S. Pat. No. 4,401,796; Caruthers, et al., U.S. Pat. Nos. 4,458,066 and 4,500,707; Beaucage, et al., *Tetrahedron Lett.*, 22:1859–1862 (1981); Matteucci; et al., *J. Am. Chem. Soc.*, 103:3185–3191 (1981); Caruthers, et al., *Genetic Engineering*, 4:1–17 (1982); Jones, chapter 2, Atkinson, et al., chapter 3, and Sproat, et al., chapter 4, in *Oligonucleotide Synthesis: A Practical Approach,* Gait (ed.), IRL Press, Washington D.C. (1984); Froehler, et al., *Tetrahedron Lett.*, 27:469–472 (1986); Froehler, et al., *Nucleic Acids Res.*, 14:5399–5407 (1986); Sinha, et al. *Tetrahedron Lett.*, 24:5843–5846 (1983); and Sinha, et al., *Nucl. Acids Res.*, 12:4539–4557 (1984) which are incorporated herein by reference.

Cationic lipids which are useful in the present invention, include, for example, DODAC, DOTMA, DDAB, DOTAP, DC-Chol and DMRIE. These lipids and related analogs, which are also useful in the present invention, have been described in co-pending U.S. Ser. No. 08/316,399; now abandoned U.S. Pat. Nos. 5,208,036, 5,264,618, 5,279,833 and 5,283,185, the disclosures of which are incorporated herein by reference. Additionally, a number of commercial preparations of cationic lipids are available and can be used in the present invention. These include, for example, LIPOFECTIN® (commercially available cationic liposomes comprising DOTMA and DOPE, from GIBCO/BRL, Grand Island, N.Y., USA); LIPOFECTAMINE® (commercially available cationic liposomes comprising DOSPA and DOPE, from GIBCO/BRL); and TRANSFECTAM® (commercially available cationic liposomes comprising DOGS from Promega Corp., Madison, Wis., USA).

An initial solution of coated plasmid-lipid complexes is formed by combining the plasmid with the cationic lipids in a detergent solution. The detergent solution is preferably an aqueous solution of a neutral detergent having a critical micelle concentration of 15–300 mM, more preferably 20–50 mM. Examples of suitable detergents include, for example, N,N'-((octanoylimino)-bis-(trimethylene))-bis-(D-gluconamide) (BIGCHAP); BRIJ 35; Deoxy-BIGCHAP; dodecylpoly(ethylene glycol) ether; Tween 20; Tween 40; Tween 60; Tween 80; Tween 85; Mega 8; Mega 9; Zwittergent® 3-08; Zwittergent® 3-10; Triton X-405; hexyl-, heptyl-, octyl- and nonyl-β-D-glucopyranoside; and heptylthioglucopyranoside; with octyl β-D-glucopyranoside being the most preferred. The concentration of detergent in the detergent solution is typically about 100 mM to about 2 M, preferably from about 200 mM to about 1.5 M.

The cationic lipids and plasmid will typically be combined to produce a charge ratio (+/−) of about 1:1 to about 20:1, preferably in a ratio of about 1:1 to about 12:1, and more preferably in a ratio of about 2:1 to about 6:1. Additionally, the overall concentration of plasmid in solution will typically be from about 25 µg/mL to about 1 mg/mL, preferably from about 25 µg/mL to about 200 µg/mL, and more preferably from about 50 µg/mL to about 100 µg/mL. The combination of plasmids and cationic lipids in detergent solution is kept, typically at room temperature, for a period of time which is sufficient for the coated complexes to form. Alternatively, the plasmids and cationic lipids can be combined in the detergent solution and warmed to temperatures of up to about 37° C. For plasmids which are particularly sensitive to temperature, the coated complexes can be formed at lower temperatures, typically down to about 4° C.

The detergent solution of the coated plasmid-lipid complexes is then contacted with non-cationic lipids to provide a detergent solution of plasmid-lipid complexes and non-cationic lipids. The non-cationic lipids which are useful in this step include, diacylphosphatidylcholine, diacylphosphatidylethanolamine, ceramide, sphingomyelin, cephalin, cardiolipin, and cerebrosides. In preferred embodiments, the non-cationic lipids are diacylphosphatidylcholine, diacylphosphatidylethanolamine, ceramide or sphingomyelin. The acyl groups in these lipids are preferably acyl groups derived from fatty acids having $C_{10}$–$C_{14}$ carbon chains. More preferably the acyl groups are lauroyl, myristoyl, palmitoyl, stearoyl or oleoyl. In particularly preferred embodiments, the non-cationic lipid will be 1,2-sn-dioleoylphosphatidylethanolamine (DOPE), palmitoyl oleoyl phosphatidylcholine (POPC) or egg phosphatidylcholine (EPC). In the most preferred embodiments, the plasmid-lipid particles will be fusogenic particles with enhanced properties in vivo and the non-cationic lipid will be DOPE. In other preferred embodiments, the non-cationic lipids will further comprise polyethylene glycol-based polymers such as PEG 2000, PEG 5000 and polyethylene glycol conjugated to ceramides, as described in co-pending U.S. Ser. No. 08/316,429, now abandoned incorporated herein by reference.

The amount of non-cationic lipid which is used in the present methods is typically about 2 to about 20 mg of total lipids to 50 μg of plasmid. Preferably the amount of total lipid is from about 5 to about 10 mg per 50 μg of plasmid.

Following formation of the detergent solution of plasmid-lipid complexes and non-cationic lipids, the detergent is removed, preferably by dialysis. The removal of the detergent results in the formation of a lipid-bilayer which surrounds the plasmid providing serum-stable plasmid-lipid particles which have a size of from about 50 nm to about 150 nm. The particles thus formed do not aggregate and are optionally sized to achieve a uniform particle size.

The serum-stable plasmid-lipid particles can be sized by any of the methods available for sizing liposomes. The sizing may be conducted in order to achieve a desired size range and relatively narrow distribution of particle sizes.

Several techniques are available for sizing the particles to a desired size. One sizing method, used for liposomes and equally applicable to the present particles is described in U.S. Pat. No. 4,737,323, incorporated herein by reference. Sonicating a particle suspension either by bath or probe sonication produces a progressive size reduction down to particles of less than about 50 nm in size. Homogenization is another method which relies on shearing energy to fragment larger particles into smaller ones. In a typical homogenization procedure, particles are recirculated through a standard emulsion homogenizer until selected particle sizes, typically between about 60 and 80 nm, are observed. In both methods, the particle size distribution can be monitored by conventional laser-beam particle size discrimination, or QELS.

Extrusion of the particles through a small-pore polycarbonate membrane or an asymmetric ceramic membrane is also an effective method for reducing particle sizes to a relatively well-defined size distribution. Typically, the suspension is cycled through the membrane one or more times until the desired particle size distribution is achieved. The particles may be extruded through successively smaller-pore membranes, to achieve a gradual reduction in size.

In another group of embodiments, the present invention provides a method for the preparation of serum-stable plasmid-lipid particles, comprising;

(a) preparing a mixture comprising cationic lipids and non-cationic lipids in an organic solvent;

(b) contacting an aqueous solution of nucleic acid with said mixture in step (a) to provide a clear single phase; and (c) removing said organic solvent to provide a suspension of plasmid-lipid particles, wherein said plasmid is encapsulated in a lipid bilayer, and said particles are stable in serum and have a size of from about 50 to about 150 nm.

The plasmids (or nucleic acids), cationic lipids and non-cationic lipids which are useful in this group of embodiments are as described for the detergent dialysis methods above.

The selection of an organic solvent will typically involve consideration of solvent polarity and the ease with which the solvent can be removed at the later stages of particle formation. The organic solvent, which is also used as a solubilizing agent, is in an amount sufficient to provide a clear single phase mixture of plasmid and lipids. Suitable solvents include chloroform, dichloromethane, diethylether, cyclohexane, cyclopentane, benzene, toluene, methanol, or other aliphatic alcohols such as propanol, isopropanol, butanol, tert-butanol, iso-butanol, pentanol and hexanol. Combinations of two or more solvents may also be used in the present invention.

Contacting the plasmid with the organic solution of cationic and non-cationic lipids is accomplished by mixing together a first solution of plasmid, which is typically an aqueous solution and a second organic solution of the lipids. One of skill in the art will understand that this mixing can take place by any number of methods, for example by mechanical means such as by using vortex mixers.

After the plasmid has been contacted with the organic solution of lipids, the organic solvent is removed, thus forming an aqueous suspension of serum-stable plasmid-lipid particles. The methods used to remove the organic solvent will typically involve evaporation at reduced pressures or blowing a stream of inert gas (e.g., nitrogen or argon) across the mixture.

The serum-stable plasmid-lipid particles thus formed will typically be sized from about 50 nm to 150 nm. To achieve further size reduction or homogeneity of size in the particles, sizing can be conducted as described above.

In other embodiments, the methods will further comprise adding nonlipid polycations which are useful to effect the transformation of cells using the present compositions. Examples of suitable nonlipid polycations include, hexadimethrine bromide (sold under the brandname POLYBRENE®, from Aldrich Chemical Co., Milwaukee, Wis., USA) or other salts of heaxadimethrine. Other suitable polycations include, for example, salts of poly-L-ornithine, poly-L-arginine, poly-L-lysine, poly-D-lysine, polyallylamine and polyethyleneimine.

In other embodiments, the polyoxyethylene conjugates which are used in the plasmid-lipid particles of the present invention can be prepared by combining the conjugating group (i.e. phosphatidic acid or phosphatidylethanolamine) with an appropriately functionalized polyoxyethylene derivative. For example, phosphatidylethanolamine can be combined with polyoxyethylene bis(p-toluenesulfonate) to provide a phosphatidylethanolamine-polyoxyethylene conjugate. See, Woodle, et al., *Biochim. Biophys. Acta* 1105:193–200 (1992), incorporated herein by reference.

The present invention also provides plasmid-lipid particles which are prepared by the methods described above. In preferred embodiments, the particles comprise a plasmid, a non-cationic lipid which is a mixture of POPC and PEG-Cer or DOPE and PEG-Cer, and a cationic lipid which is DODAC.

IV. Pharmaceutical Preparations

The plasmid-lipid particles of the present invention can be administered either alone or in mixture with a physiologically-acceptable carrier (such as physiological saline or phosphate buffer) selected in accordance with the route of administration and standard pharmaceutical practice.

Pharmaceutical compositions comprising the plasmid-lipid particles of the invention are prepared according to standard techniques and further comprise a pharmaceutically acceptable carrier. Generally, normal saline will be employed as the pharmaceutically acceptable carrier. Other suitable carriers include, e.g., water, buffered water, 0.4% saline, 0.3% glycine, and the like, including glycoproteins for enhanced stability, such as albumin, lipoprotein, globulin, etc. These compositions may be sterilized by conventional, well known sterilization techniques. The resulting aqueous solutions may be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc. Additionally, the particle suspension may include lipid-protective agents which protect lipids against free-radical and lipid-peroxidative damages on storage. Lipophilic free-radical quenchers, such as alphatocopherol and water-soluble iron-specific chelators, such as ferrioxamine, are suitable.

The concentration of particles in the pharmaceutical formulations can vary widely, i.e., from less than about 0.05%, usually at or at least about 2–5% to as much as 10 to 30% by weight and will be selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, particles composed of irritating lipids may be diluted to low concentrations to lessen inflammation at the site of administration. For diagnosis, the amount of particles administered will depend upon the particular label used, the disease state being diagnosed and the judgement of the clinician but will generally be between about 0.01 and about 50 mg per kilogram of body weight, preferably between about 0.1 and about 5 mg/kg of body weight.

As noted above, it is often desirable to include polyethylene glycol (PEG), PEG-ceramide, or ganglioside GM1-modified lipids to the particles. Addition of such components prevents particle aggregation and provides a means for increasing circulation lifetime and increasing the delivery of the plasmid-lipid particles to the target tissues. Typically, the concentration of the PEG, PEG-ceramide or GMl-modified lipids in the particle will be about 1–15%.

Overall particle charge is also an important determinant in particle clearance from the blood, with negatively charged complexes being taken up more rapidly by the reticuloendothelial system (Juliano, *Biochem. Biophys. Res. Commun.* 63:651 (1975)) and thus having shorter half-lives in the bloodstream. Particles with prolonged circulation half-lives are typically desirable for therapeutic and diagnostic uses. For instance, particles which can be maintained from 8, 12, or up to 24 hours in the bloodstream are particularly preferred.

In another example of their use, plasmid-lipid particles can be incorporated into a broad range of topical dosage forms including but not limited to gels, oils, emulsions and the like. For instance, the suspension containing the plasmid-lipid particles can be formulated and administered as topical creams, pastes, ointments, gels, lotions and the like.

The present invention also provides plasmid-lipid particles in kit form. The kit will typically be comprised of a container which is compartmentalized for holding the various elements of the kit. The kit will contain the compositions of the present inventions, preferably in dehydrated form, with instructions for their rehydration and administration. In still other embodiments, the particles and/or compositions comprising the particles will have a targeting moiety attached to the surface of the particle. Methods of attaching targeting moieties (e.g., antibodies, proteins) to lipids (such as those used in the present particles) are known to those of skill in the art.

Dosage for the plasmid-lipid particle formulation will depend on the ratio of nucleic acid to lipid and the administrating physician's opinion based on age, weight, and condition of the patient.

V. Administration of Plasmid-Lipid Particle Formulations

The serum-stable plasmid-lipid particles of the present invention are useful for the introduction of plasmids into cells. Accordingly, the present invention also provides methods for introducing a plasmid into a cell. The methods are carried out in vitro or in vivo by first forming the particles as described above, then contacting the particles with the cells for a period of time sufficient for transfection to occur.

The particles of the present invention can be adsorbed to almost any cell type. Once adsorbed, the particles can either be endocytosed by a portion of the cells, exchange lipids with cell membranes, or fuse with the cells. Transfer or incorporation of the nucleic acid portion of the particle can take place via any one of these pathways. In particular, when fusion takes place, the particle membrane is integrated into the cell membrane and the contents of the particle combine with the intracellular fluid. Contact between the cells and the plasmid-lipid particles, when carried out in vitro, will take place in a biologically compatible medium. The concentration of particles can vary widely depending on the particular application, but is generally between about 1 $\mu$mol and about 10 mmol. Treatment of the cells with the plasmid-lipid particles will generally be carried out at physiological temperatures (about 37° C.) for periods of time of from about 1 to 6 hours, preferably of from about 2 to 4 hours. For in vitro applications, the delivery of nucleic acids can be to any cell grown in culture, whether of plant or animal origin, vertebrate or invertebrate, and of any tissue or type. In preferred embodiments, the cells will be animal cells, more preferably mammalian cells, and most preferably human cells.

In one group of preferred embodiments, a plasmid-lipid particle suspension is added to 60–80% confluent plated cells having a cell density of from about $10^3$ to about $10^5$ cells/mL, more preferably about $2\times10^4$ cells/mL. The concentration of the suspension added to the cells is preferably of from about 0.01 to 0.2 $\mu$g/mL, more preferably about 0.1 $\mu$g/mL.

Typical applications include using well known transfection procedures to provide intracellular delivery of DNA or mRNA sequences which- code for therapeutically useful polypeptides. However, the compositions can also be used for the delivery of the expressed gene product or protein itself. In this manner, therapy is provided for genetic diseases by supplying deficient or absent gene products (i.e., for Duchenne's dystrophy, see Kunkel, et al., *Brit. Med. Bull.* 45(3):630–643 (1989), and for cystic fibrosis, see Goodfellow, Nature 341:102–103 (1989)). Other uses for the compositions of the present invention include introduction of antisense oligonucleotides in cells (see, Bennett, et al., *Mol. Pharm.* 41:1023–1033 (1992)).

Alternatively, the compositions of the present invention can also be used for the transfection of cells in vivo, using methods which are known to those of skill in the art. In particular, Zhu, et al., Science 261:209–211 (1993), incorporated herein by reference, describes the intravenous delivery of cytomegalovirus (CMV)-chloramphenicol acetyltransferase (CAT) expression plasmid using DOTMA-DOPE complexes. Hyde, et al., Nature 362:250–256 (1993), incorporated herein by reference, describes the delivery of the cystic fibrosis transmembrane conductance regulator (CFTR) gene to epithelia of the airway and to alveoli in the lung of mice, using liposomes. Brigham, et al., Am. J. Med. Sci. 298:278–281 (1989), incorporated herein by reference, describes the in vivo transfection of lungs of mice with a functioning prokaryotic gene encoding the intracellular enzyme, chloramphenicol acetyltransferase (CAT).

For in vivo administration, the pharmaceutical compositions are preferably administered parenterally, i.e., intraarticularly, intravenously, intraperitoneally, subcutaneously, or intramuscularly. More preferably, the pharmaceutical compositions are administered intravenously or intraperitoneally by a bolus injection. For example, see Stadler, et al., U.S. Pat. No. 5,286,634, which is incorporated herein by reference. Intracellular nucleic acid delivery has also been discussed in Straubringer, et al., METHODS IN ENZYMOLOGY, Academic Press, New York. 101:512–527 (1983); Mannino, et al., Biotechniques 6:682–690 (1988); Nicolau, et al., Crit. Rev. Ther. Drug Carrier Syst. 6:239–271 (1989), and Behr, Acc. Chem. Res. 26:274–278 (1993). Still other methods of administering lipid-based therapeutics are described in, for example, Rahman et al., U.S. Pat. No. 3,993,754; Sears, U.S. Pat. No. 4,145,410; Papahadjopoulos et al., U.S. Pat. No. 4,235,871; Schneider, U.S. Pat. No. 4,224,179; Lenk et al., U.S. Pat. No. 4,522,803; and Fountain et al., U.S. Pat. No. 4,588,578.

In other methods, the pharmaceutical preparations may be contacted with the target tissue by direct application of the preparation to the tissue. The application may be made by topical, "open" or "closed" procedures. By "topical", it is meant the direct application of the pharmaceutical preparation to a tissue exposed to the environment, such as the skin, oropharynx, external auditory canal, and the like. "Open" procedures are those procedures which include incising the skin of a patient and directly visualizing the underlying tissue to which the pharmaceutical preparations are applied. This is generally accomplished by a surgical procedure, such as a thoracotomy to access the lungs, abdominal laparotomy to access abdominal viscera, or other direct surgical approach to the target tissue. "Closed" procedures are invasive procedures in which the internal target tissues are not directly visualized, but accessed via inserting instruments through small wounds in the skin. For example, the preparations may be administered to the peritoneum by needle lavage. Likewise, the pharmaceutical preparations may be administered to the meninges or spinal cord by infusion during a lumbar puncture followed by appropriate positioning of the patient as commonly practiced for spinal anesthesia or meamide imaging of the spinal cord. Alternatively, the preparations may be administered through endoscopic devices.

The plasmid-lipid particles can also be administered in an aerosol inhaled into the lungs (see, Brigham, et al., Am. J. Sci. 298(4):278–281 (1989)) or by direct injection at the site of disease (Culver, HUMAN GENE THERAPY, MaryAnn Liebert, Inc., Publishers, New York. pp.70–71(1994)).

The methods of the present invention may be practiced in a variety of hosts. Preferred hosts include mammalian species, such as humans, non-human primates, dogs, cats, cattle, horses, sheep, and the like.

VI. Examples

The following examples are offered solely for the purposes of illustration, and are intended neither to limit nor to define the invention. In each of these examples, the term "DNA" or "plasmid" refers to the plasmid pCMV4-CAT.

EXAMPLE 1

This example illustrates the encapsulation of a plasmid in a lipid bilayer system using either a reverse-phase method or a detergent dialysis method.

Reverse Phase Method pCMV4-CAT plasmid (50 $\mu$g) was encapsulated in a lipid bilayer which was constructed using 20 mg POPC:PEG-Cer-$C_{20}$ (95:5 mole % ratio) with between 0 and 0.3 mg DODAC. The encapsulation method utilized a modification of the classical reverse phase method for entrapment. Specifically, 1.050 mL of chloroform:methanol in a 1:2.1 mole % ratio was added to a lipid film containing 2 $\mu$L of $^{14}$C-cholesteryl hexadecyl ether (6.66 $\mu$L/$\mu$Ci). This was followed by the addition of 220 $\mu$L $H_2O$ and 33 $\mu$L $^3$H-pCMV4-CAT plasmid (158,000 dpm/$\mu$L; 1.5 mg/mL). This combination provided a clear single phase. The $CHCl_3$ and most of the methanol were removed under a stream of nitrogen while vortexing the mixture. The resulting 250 $\mu$L suspension of encapsulated plasmid was diluted with 1 mL of $H_2O$ and extruded 5 times through one 400 nm filter followed by extrusion 5 times through one 200 nm filter. The resulting vesicle size was approximately 150 to 200 nm in diameter.

Detergent Dialysis Method pCMVCAT (50 $\mu$g consisting of 20 $\mu$L of $^3$H-pCMV4-CAT and 30 $\mu$L of cold pCMV4-CAT at a concentration of 1 mg/mL, "plasmid") was incubated with DODAC at various DODAC:plasmid charge ratios in 100 $\mu$L of 1M n-octyl-$\beta$-D-glucopyranoside and 400 $\mu$L $H_2O$ for 30 min at room temperature. The resulting plasmid:DODAC mixture was added to a suspension of 5 mg POPC:PEG-Cer($C_{20}$) or 10 mg DOPE:PBG-Cer($C_{20}$) (containing 1 $\mu$L $^{14}$C-cholesteryl hexadecyl ether; 6.66 $\mu$L/$\mu$Ci) in 100 $\mu$L of 1 M n-octyl-$\beta$-D-glucopyranoside and 400 $\mu$L of $H_2O$). The amounts used for each lipid to achieve a desired charge ratio are shown in Tables 1–3. The suspension was dialysed against HBS at pH 7.4 overnight. The resulting encapsulated plasmid can be used without further sizing.

TABLE 1

Calculation of % DODAC in vesicles for any given DODAC:DNA charge ratio as a function of total mg of lipid

| Lipid (mg) | DODAC:DNA | DNA microgram | POPC % | DODAC % | PEGCer % | POPC mg | DODAC mg | PEGCer mg | total lipid micromole |
|---|---|---|---|---|---|---|---|---|---|
| 20 | 1 | 50 | 89.25979 | 0.740207 | 10 | 14.09342 | 0.0895 | 5.817079 | 20.77528 |
| 20 | 2 | 50 | 88.52161 | 1.478393 | 10 | 13.99597 | 0.179 | 5.82503 | 20.80368 |

TABLE 1-continued

Calculation of % DODAC in vesicles for any given DODAC:DNA charge ratio as a function of total mg of lipid

| Lipid (mg) | DODAC:DNA | DNA microgram | POPC % | DODAC % | PEGCer % | POPC mg | DODAC mg | PEGCer mg | total lipid micromole |
|---|---|---|---|---|---|---|---|---|---|
| 20 | 3 | 50 | 87.78543 | 2.214567 | 10 | 13.89852 | 0.2685 | 5.83298 | 20.83207 |
| 20 | 4 | 50 | 87.05126 | 2.948737 | 10 | 13.80107 | 0.358 | 5.840931 | 20.86047 |
| 20 | 5 | 50 | 86.31909 | 3.68091 | 10 | 13.70362 | 0.4475 | 5.848882 | 20.88886 |
| 20 | 6 | 50 | 85.5889 | 4.411096 | 10 | 13.60617 | 0.537 | 5.856832 | 20.91726 |
| 20 | 7 | 50 | 84.8607 | 5.139302 | 10 | 13.50872 | 0.6265 | 5.864783 | 20.94565 |
| 20 | 8 | 50 | 84.13446 | 5.865537 | 10 | 13.41127 | 0.716 | 5.872734 | 20.97405 |
| 20 | 9 | 50 | 83.41019 | 6.589808 | 10 | 13.31382 | 0.8055 | 5.880684 | 21.00244 |
| 20 | 10 | 50 | 82.68788 | 7.312122 | 10 | 13.21637 | 0.895 | 5.888635 | 21.03084 |
| 20 | 11 | 50 | 81.96751 | 8.03249 | 10 | 13.11891 | 0.9845 | 5.896585 | 21.05923 |
| 20 | 12 | 50 | 81.24908 | 8.750917 | 10 | 13.02146 | 1.074 | 5.904536 | 21.08763 |
| 20 | 13 | 50 | 80.53259 | 9.467412 | 10 | 12.92401 | 1.1635 | 5.912487 | 21.11602 |
| 20 | 14 | 50 | 79.81802 | 10.18198 | 10 | 12.82656 | 1.253 | 5.920437 | 21.14442 |
| 20 | 15 | 50 | 79.10536 | 10.89464 | 10 | 12.72911 | 1.3425 | 5.928388 | 21.17281 |
| 20 | 16 | 50 | 78.39462 | 11.60538 | 10 | 12.63166 | 1.432 | 5.936339 | 21.20121 |
| 20 | 17 | 50 | 77.68578 | 12.31422 | 10 | 12.53421 | 1.5215 | 5.944289 | 21.2296 |
| 20 | 18 | 50 | 76.97883 | 13.02117 | 10 | 12.43676 | 1.611 | 5.95224 | 21.258 |
| 20 | 19 | 50 | 76.27376 | 13.72624 | 10 | 12.33931 | 1.7005 | 5.96019 | 21.28639 |
| 20 | 20 | 50 | 75.57058 | 14.42942 | 10 | 12.24186 | 1.79 | 5.968141 | 21.31479 |

TABLE 2

Calculation of % DODAC in vesicles for any given DODAC:DNA charge ratio as a function of total mg of lipid

| Lipid (mg) | DODAC:DNA | DNA microgram | POPC % | DODAC % | PEGCer % | POPC mg | DODAC mg | PEGCer mg | total lipid micromole |
|---|---|---|---|---|---|---|---|---|---|
| 5 | 1 | 50 | 87.05126 | 2.948737 | 10 | 3.450267 | 0.0895 | 1.460233 | 5.215117 |
| 5 | 2 | 50 | 84.13446 | 5.865537 | 10 | 3.352817 | 0.179 | 1.468183 | 5.243512 |
| 5 | 3 | 50 | 81.24908 | 8.750917 | 10 | 3.255366 | 0.2685 | 1.476134 | 5.271907 |
| 5 | 4 | 50 | 78.39462 | 11.60538 | 10 | 3.157915 | 0.358 | 1.484085 | 5.300302 |
| 5 | 5 | 50 | 75.57058 | 14.42942 | 10 | 3.060465 | 0.4475 | 1.492035 | 5.328697 |
| 5 | 6 | 50 | 72.77647 | 17.22353 | 10 | 2.963014 | 0.537 | 1.499986 | 5.357092 |
| 5 | 7 | 50 | 70.01183 | 19.98817 | 10 | 2.865563 | 0.6265 | 1.507937 | 5.385488 |
| 5 | 8 | 50 | 67.27619 | 22.72381 | 10 | 2.768113 | 0.716 | 1.515887 | 5.413883 |
| 5 | 9 | 50 | 64.56909 | 25.43091 | 10 | 2.670662 | 0.8055 | 1.523838 | 5.442278 |
| 5 | 10 | 50 | 61.8901 | 28.1099 | 10 | 2.573212 | 0.895 | 1.531788 | 5.470673 |
| 5 | 11 | 50 | 59.23877 | 30.76123 | 10 | 2.475761 | 0.9845 | 1.539739 | 5.499068 |
| 5 | 12 | 50 | 56.61469 | 33.38531 | 10 | 2.37831 | 1.074 | 1.54769 | 5.527463 |
| 5 | 13 | 50 | 54.01742 | 35.98258 | 10 | 2.28086 | 1.1635 | 1.55564 | 5.555858 |
| 5 | 14 | 50 | 51.44657 | 38.55343 | 10 | 2.183409 | 1.253 | 1.563591 | 5.584253 |
| 5 | 15 | 50 | 48.90173 | 41.09827 | 10 | 2.085959 | 1.3425 | 1.571541 | 5.612648 |
| 5 | 16 | 50 | 46.38252 | 43.61748 | 10 | 1.988508 | 1.432 | 1.579492 | 5.641043 |
| 5 | 17 | 50 | 43.88853 | 46.11147 | 10 | 1.891057 | 1.5215 | 1.587443 | 5.669438 |
| 5 | 18 | 50 | 41.41941 | 48.58059 | 10 | 1.793607 | 1.611 | 1.595393 | 5.697833 |
| 5 | 19 | 50 | 38.97477 | 51.02523 | 10 | 1.696156 | 1.7005 | 1.603344 | 5.726228 |
| 5 | 20 | 50 | 36.55426 | 53.44574 | 10 | 1.598705 | 1.79 | 1.611295 | 5.754623 |

TABLE 3

Calculation of % DODAC in vesicles for any given DODAC:DNA charge ratio as a function of total mg of lipid

| Lipid (mg) | DODAC:DNA | DNA microgram | DOPE % | DODAC % | PEGCer % | DOPE mg | DODAC mg | PEGCer mg | total lipid micromole |
|---|---|---|---|---|---|---|---|---|---|
| 10 | 1 | 50 | 88.54333 | 1.456667 | 10 | 6.954544 | 0.0895 | 2.955956 | 10.55698 |
| 10 | 2 | 50 | 87.09389 | 2.906111 | 10 | 6.857699 | 0.179 | 2.963301 | 10.58322 |
| 10 | 3 | 50 | 85.65161 | 4.348388 | 10 | 6.760853 | 0.2685 | 2.970647 | 10.60945 |
| 10 | 4 | 50 | 84.21645 | 5.783549 | 10 | 6.664007 | 0.358 | 2.977993 | 10.63569 |
| 10 | 5 | 50 | 82.78835 | 7.211648 | 10 | 6.567162 | 0.4475 | 2.985338 | 10.66192 |
| 10 | 6 | 50 | 81.36726 | 8.632736 | 10 | 6.470316 | 0.537 | 2.992684 | 10.68816 |
| 10 | 7 | 50 | 79.95314 | 10.04686 | 10 | 6.37347 | 0.6265 | 3.00003 | 10.71439 |
| 10 | 8 | 50 | 78.54591 | 11.45409 | 10 | 6.276625 | 0.716 | 3.007375 | 10.74063 |
| 10 | 9 | 50 | 77.14555 | 12.85445 | 10 | 6.179779 | 0.8055 | 3.014721 | 10.76686 |

TABLE 3-continued

Calculation of % DODAC in vesicles for any given DODAC:DNA charge ratio as a function of total mg of lipid

| Lipid (mg) | DODAC:DNA | DNA microgram | DOPE % | DODAC % | PEGCer % | DOPE mg | DODAC mg | PEGCer mg | total lipid micromole |
|---|---|---|---|---|---|---|---|---|---|
| 10 | 10 | 50 | 75.752 | 14.248 | 10 | 6.082933 | 0.895 | 3.022067 | 10.7931 |
| 10 | 11 | 50 | 74.3652 | 15.6348 | 10 | 5.986088 | 0.9845 | 3.029412 | 10.81933 |
| 10 | 12 | 50 | 72.98511 | 17.01489 | 10 | 5.889242 | 1.074 | 3.036758 | 10.84556 |
| 10 | 13 | 50 | 71.61168 | 18.38832 | 10 | 5.792396 | 1.1635 | 3.044104 | 10.8718 |
| 10 | 14 | 50 | 76.24487 | 19.75513 | 10 | 5.69555 | 1.253 | 3.05145 | 10.89803 |
| 10 | 15 | 50 | 68.88462 | 21.11538 | i6 | 5.598705 | 1.3425 | 3.058795 | 10.92427 |
| 10 | 16 | 50 | 67.53089 | 22.46911 | 10 | 5.501859 | 1.432 | 3.066141 | 10.9505 |
| 10 | 17 | 50 | 66.18362 | 23.81638 | 10 | 5.405013 | 1.5215 | 3.073487 | 10.97674 |
| 10 | 18 | 50 | 64.84279 | 25.15721 | 10 | 5.308168 | 1.611 | 3.080832 | 11.00297 |
| 10 | 19 | 50 | 63.50833 | 26.49167 | 10 | 5.211322 | 1.7005 | 3.088178 | 11.02921 |
| 10 | 20 | 50 | 62.1802 | 27.8198 | 10 | 5.114476 | 1.79 | 3.095524 | 11.05544 |

EXAMPLE 2

This example illustrates the level of plasmid "protection" from external medium using anion exchange chromatography.

The extent of encapsulation or protection of the plasmid from the external medium was assessed by anion exchange chromatography as follows: a 50 μL aliquot of each sample was eluted on a DEAE Sepharose CL-6B column and the fractions were assessed for both $^3$H-plasmid and $^{14}$C-lipid by scintillation counting. Any exposed negative charges, such as those present on DNA molecules will bind to the anion exchange column and will not elute with the $^{14}$C-lipid. DNA which has its negative charge "protected" or non-exposed will not bind to the ion exchange resin and will elute with the $^{14}$C-lipid.

Reverse Phase Method (Particles with POPC:DODAC:PEG-Cer($C_{20}$))

Figure 4:
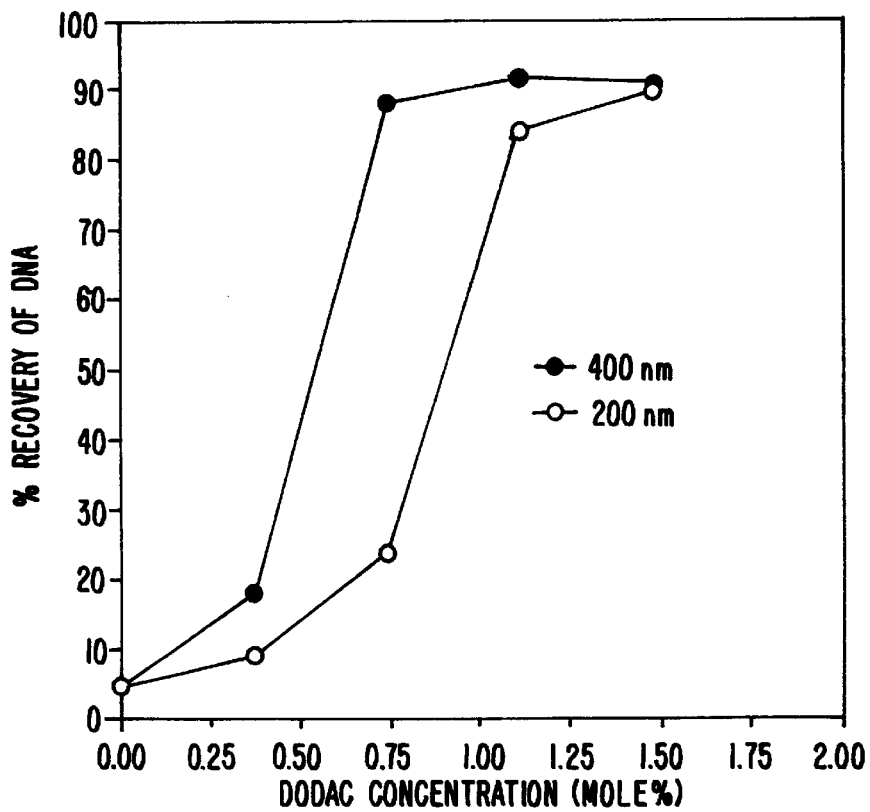
FIG. 4 illustrates the recovery of $^3$H-DNA from encapsulated particles following the reverse-phase preparation of the particles and extrusion through a 400 nm filter and a 200 nm filter. Lipid composition is POPC:DODAC:PEG-Cer ($C_{20}$) in proportions as shown in Table 1.
Figure 5:
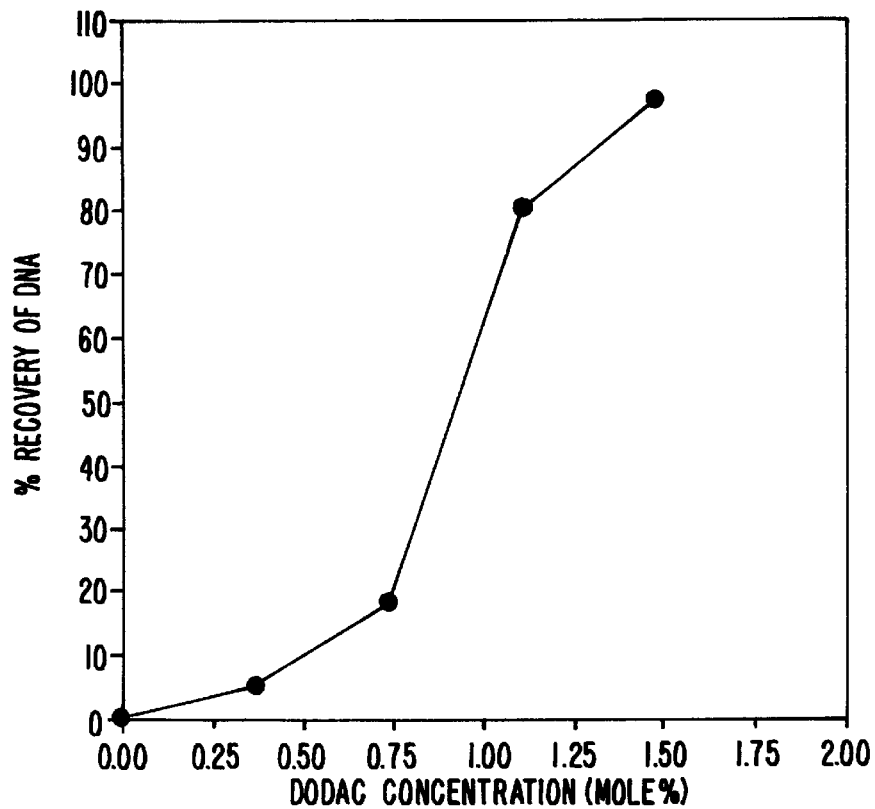
FIG. 5 illustrates the recovery of $^3$H-DNA from particles prepared using a reverse-phase procedure. The particles were extruded through a 200 nm filter and eluted on a DEAE Sepharose CL-6B anion exchange column. The percent recovery reported is based on the amount recovered after filtration. Lipid composition is as in FIG. 4.
Figure 7:
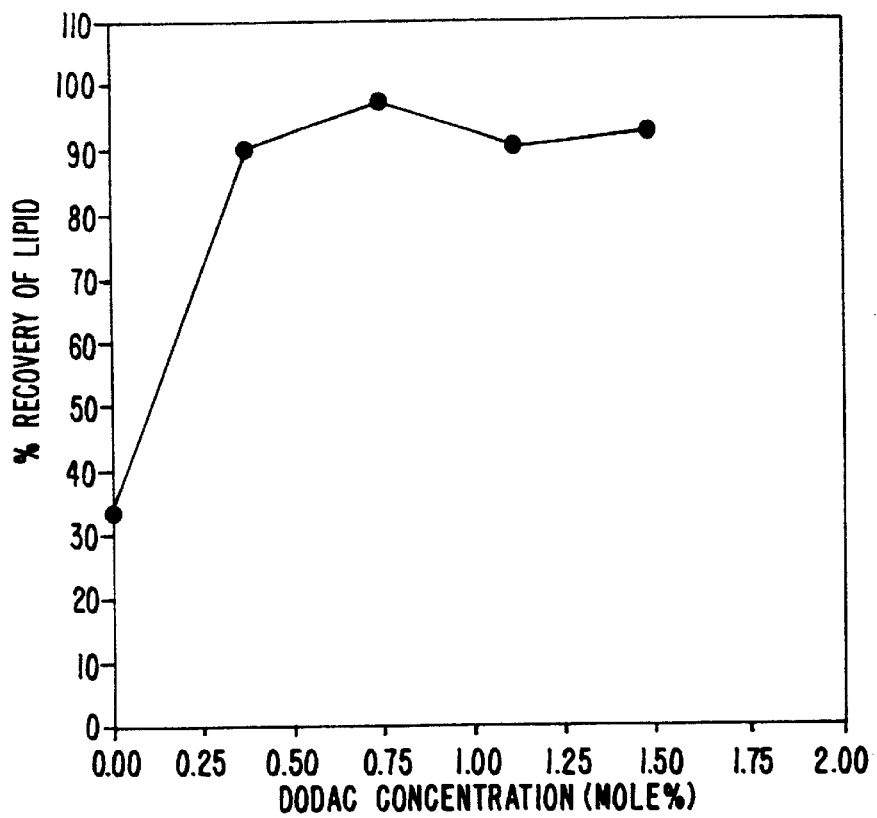
FIG. 7 illustrates the recovery of $^{14}$C-lipid from particles prepared using a reverse-phase procedure. The particles were extruded through a 200 nm filter and eluted on a DEAE Sepharose CL-6B anion exchange column. The percent recovery reported is based on the amount recovered after filtration. Lipid composition is as in FIG. 4.
Figure 6:
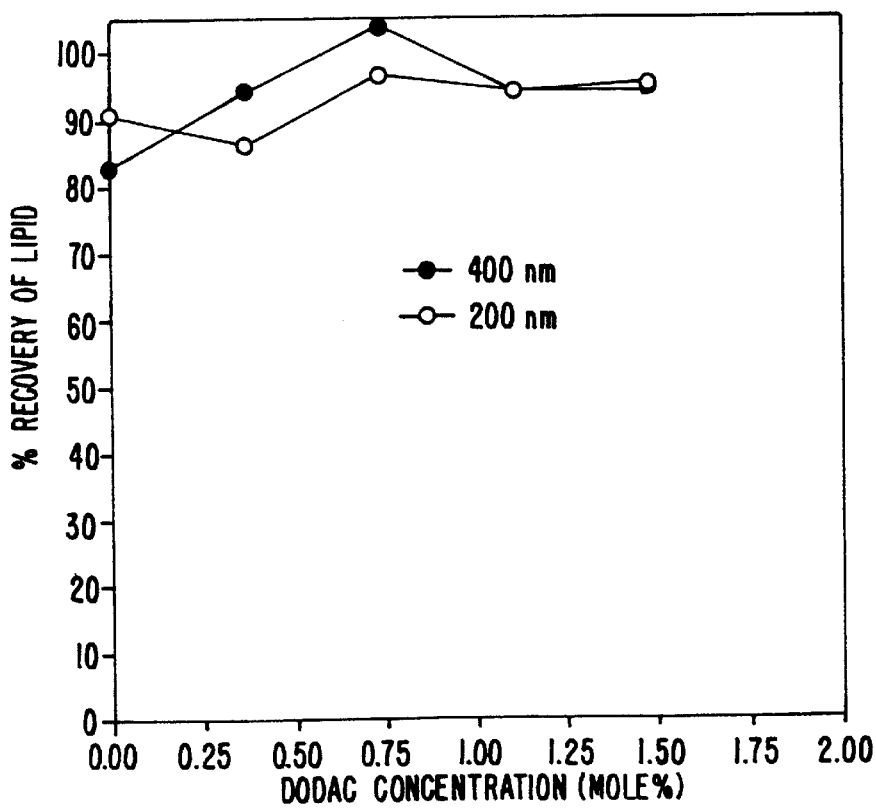
FIG. 6 illustrates the recovery of $^{14}$C-lipid from encapsulated particles following the reverse-phase preparation of the particles and extrusion through a 400 nm filter and a 200 nm filter. Lipid composition is as in FIG. 4.

FIG. 4 presents the results describing the relationship between DODAC:plasmid charge ratio (see Table 1 for amounts of POPC, DODAC and PEG-Cer($C_{20}$) using 20 mg total lipid) and percent recovery of plasmid after extrusion through a 400 nm filter and a 200 nm filter. An increase in percent plasmid recovered was observed corresponding to an increase in DODAC:plasmid charge ratio. No plasmid was recovered in the absence of DODAC while, at a DODAC:plasmid charge ratio of 2:1, 90% of the plasmid was recovered after extrusion through a 400 nm filter and 70% of the plasmid was recovered after extrusion through a 200 nm filter. Nearly 100% of the plasmid recovered from extrusion through a 200 nm filter was recovered by anion exchange chromatography (see FIG. 5) suggesting that all of the recovered plasmid was encapsulated. This corresponded to an overall encapsulation efficiency of about 70%. Lipid recoveries after extrusion and anion exchange chromatography were 90% after extrusion through a 400 nm filter and 70% after extrusion through a 200 nm filter (see FIG. 6). Of the 70% lipid recovered after extrusion through a 200 nm filter, nearly 100% was recovered after anion exchange chromatography (see FIG. 7). Lipid and plasmid recovery after extrusion and anion exchange chromatography were nearly identical.

Dialysis Method (Particles with POPC:DODAC:PEG-Cer ($C_{20}$))

Figure 8:
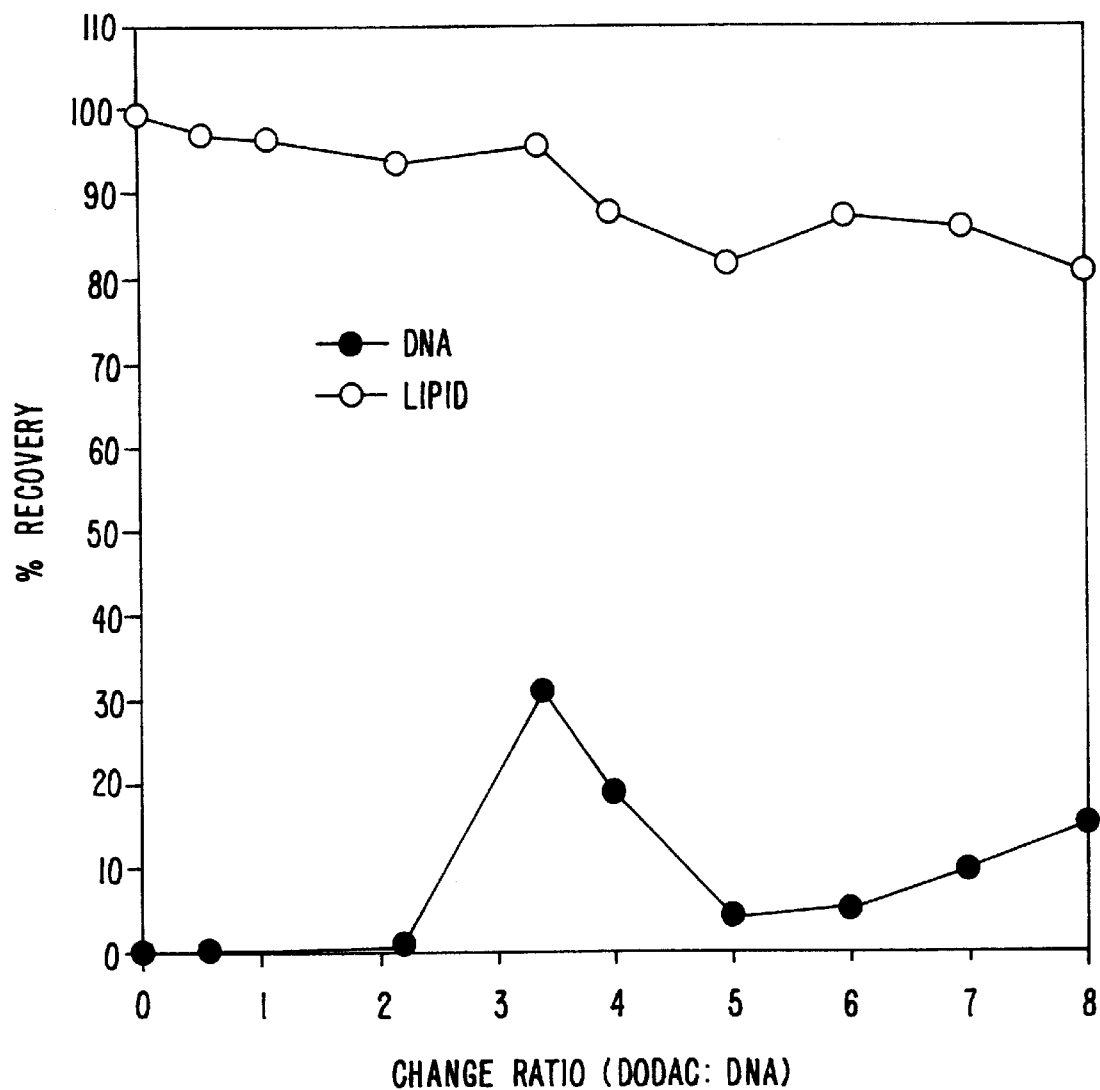
FIG. 8 illustrates recovery of $^3$H-DNA and $^{14}$C-lipids from particles prepared by detergent dialysis after elution on a DEAE Sepharose CL-6B anion exchange column in HBS, pH 7.4. Lipid composition is POPC:DODAC:PEG-Cer($C_{20}$) in proportions as shown in Table 2.

FIG. 8 provides the results which illustrate the effect of DODAC:plasmid charge ratio on the percent recovery of lipid and plasmid from anion exchange chromatography following preparation of the particles using the detergent dialysis method of Example 1 (amounts of lipids are provided in Table 2 for 5 mg total lipid compositions). Significant protection was observed over a DODAC:plasmid charge ratio of about 3:1 to 5:1. Also, it appears that significant protection of the plasmid is achieved at a DODAC:plasmid charge ratio of about 8:1. The recovery of lipid decreased from 100% in the absence of DODAC to about 85% at a DODAC:plasmid charge ratio of 8:1.

Dialysis Method (particles with DOPE:DODAC:PEG-Cer($C_{20}$))

Figure 9:
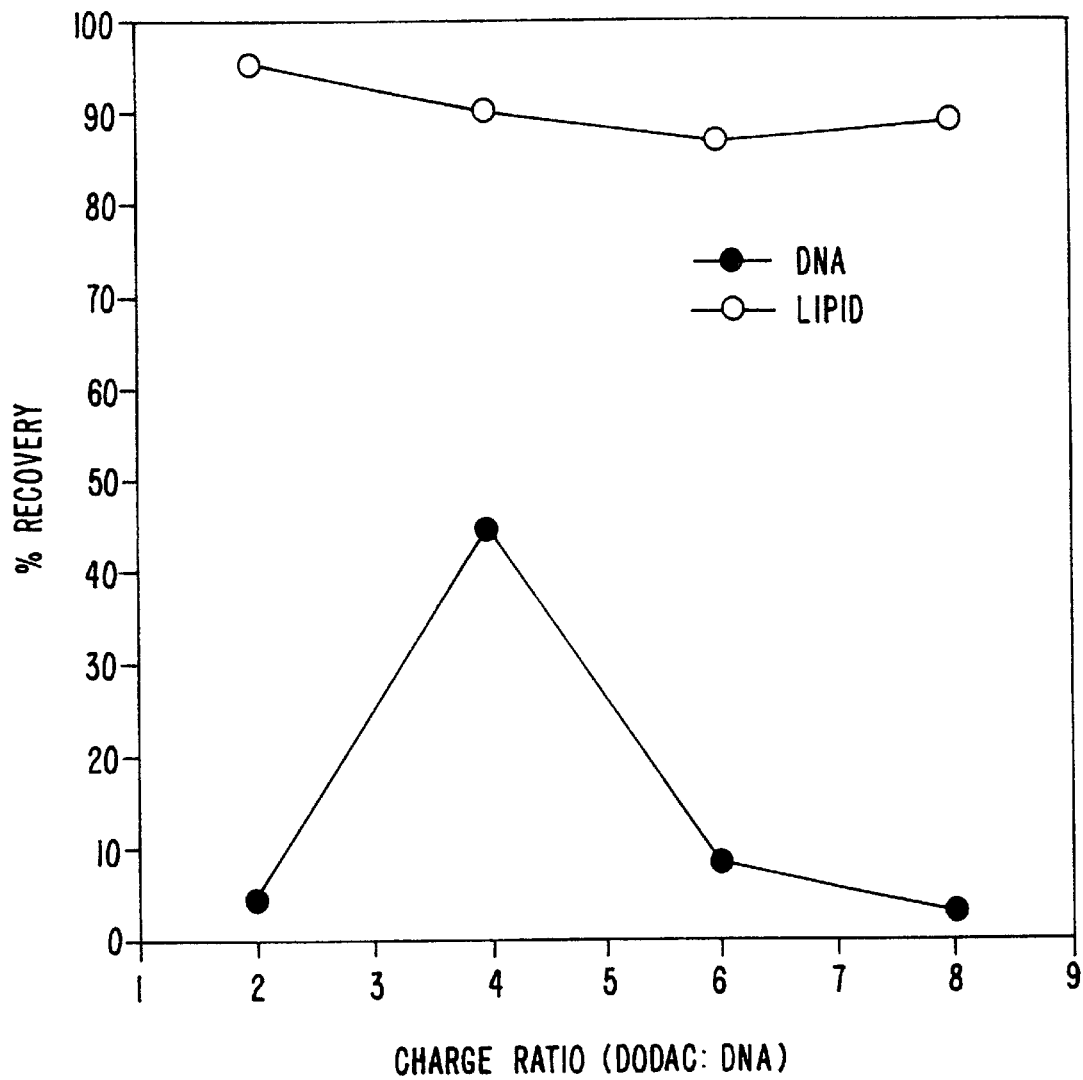
FIG. 9 illustrates recovery of $^3$H-DNA and $^{14}$C-lipids from particles prepared by detergent dialysis after elution on a DEAE Sepharose CL-6B anion exchange column in HBS, pH 7.4. Lipid composition is DOPE:DODAC:PEG-Cer($C_{20}$) in proportions as shown in Table 3.

In a similar manner to that described for the POPC-containing particles, the fusogenic lipid composition DOPE:DODAC:PEG-Cer($C_{20}$) was assessed by anion exchange chromatography. Aliquots (50 μL) of the plasmid-lipid particles (prepared by detergent dialysis, using the amounts provided in Table 3) were eluted on a DEAE Sepharose CL-6B column. FIG. 9 provides the results and illustrates the relationship between the DODAC:DNA charge ratio and % recovery of lipid and DNA for particles using 10 mg of total lipid. DNA encapsulation occurred at a DODAC:DNA charge ratio of 4:1.

EXAMPLE 3

This example illustrates the serum stability achieved using plasmid:lipid particles prepared by the methods of Example 1.

To establish the serum stability of the plasmid:lipid particles, aliquots of the particle mixtures prepared according to both the reverse phase and dialysis methods of Example 1 were incubated in mouse serum (Cedar Lane) for 15 min and for 30 min at 37° C. Prior to incubation, the lipid associated plasmid was eluted on a DEAE Sepharose CL-6B column to remove unencapsulated plasmid. Following incubation, an aliquot of the incubation mixture was eluted in HBS on a Sepharose CL-4B column.

Figure 10:
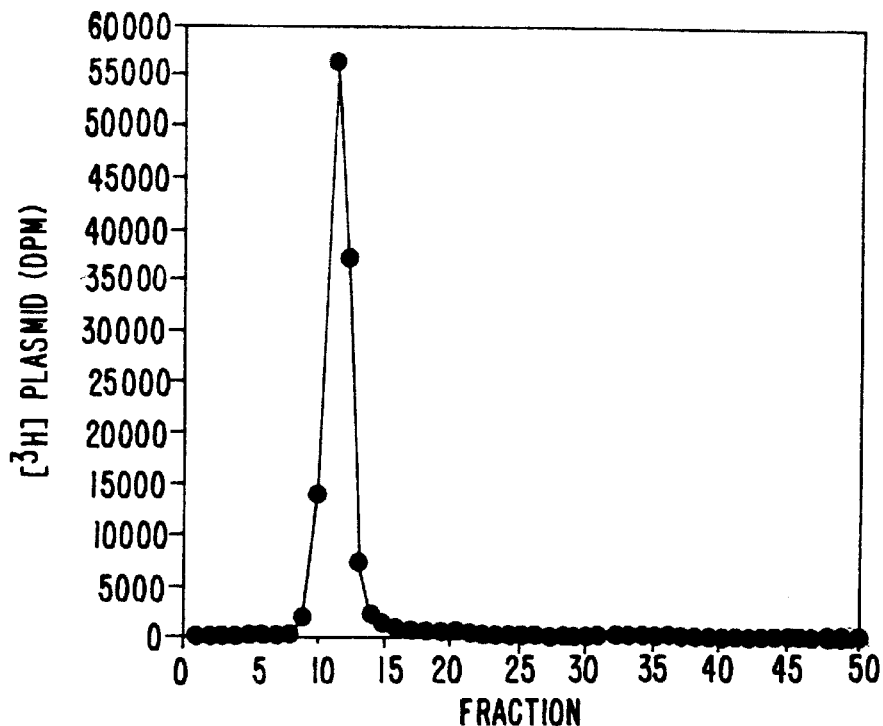
FIG. 10 provides an elution profile of free $^3$H-DNA (pCMV4-CAT) on a Sepharose CL-4B column in HBS, pH 7.4.
Figure 11:
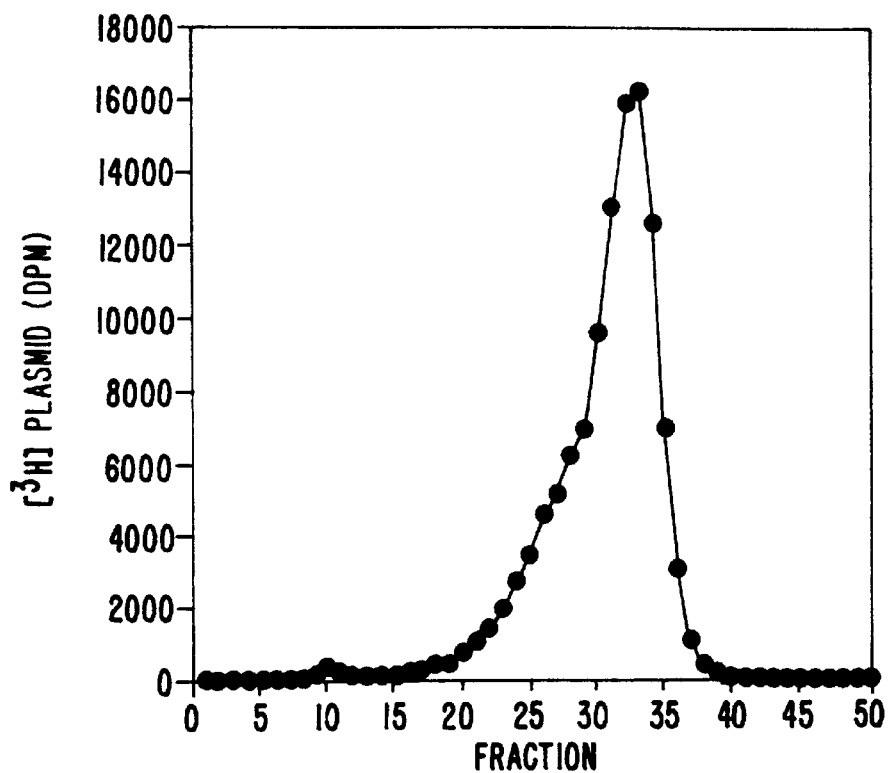
FIG. 11 provides an elution profile of free $^3$H-DNA (pCMV4-CAT) on a Sepharose CL-4B column in HBS, pH 7.4, after incubation in 80% mouse serum for 30 min at 37° C.

As a control, 1.5 mg of free $^3$H-pCMV4-CAT was eluted on a Sepharose CL-4B column in HBS, pH 7.4 (see FIG. 10). For comparison, 1.5 mg of free $^3$H-pCMV4-CAT was incubated in 500 μL of mouse serum at 37° C. for 30 min and eluted in the same manner (see FIG. 11). Note that in FIG. 10, the free plasmid eluted in the void volume of the column while, in FIG. 11, the plasmid incubated in serum eluted in the included volume suggesting that the plasmid had been digested by serum enzymes.

Serum Stability of Plasmid-Lipid Particles Prepared by Reverse Phase (particles prepared from POPC:DODAC:PEG-Cer($C_2$))

Figure 12:
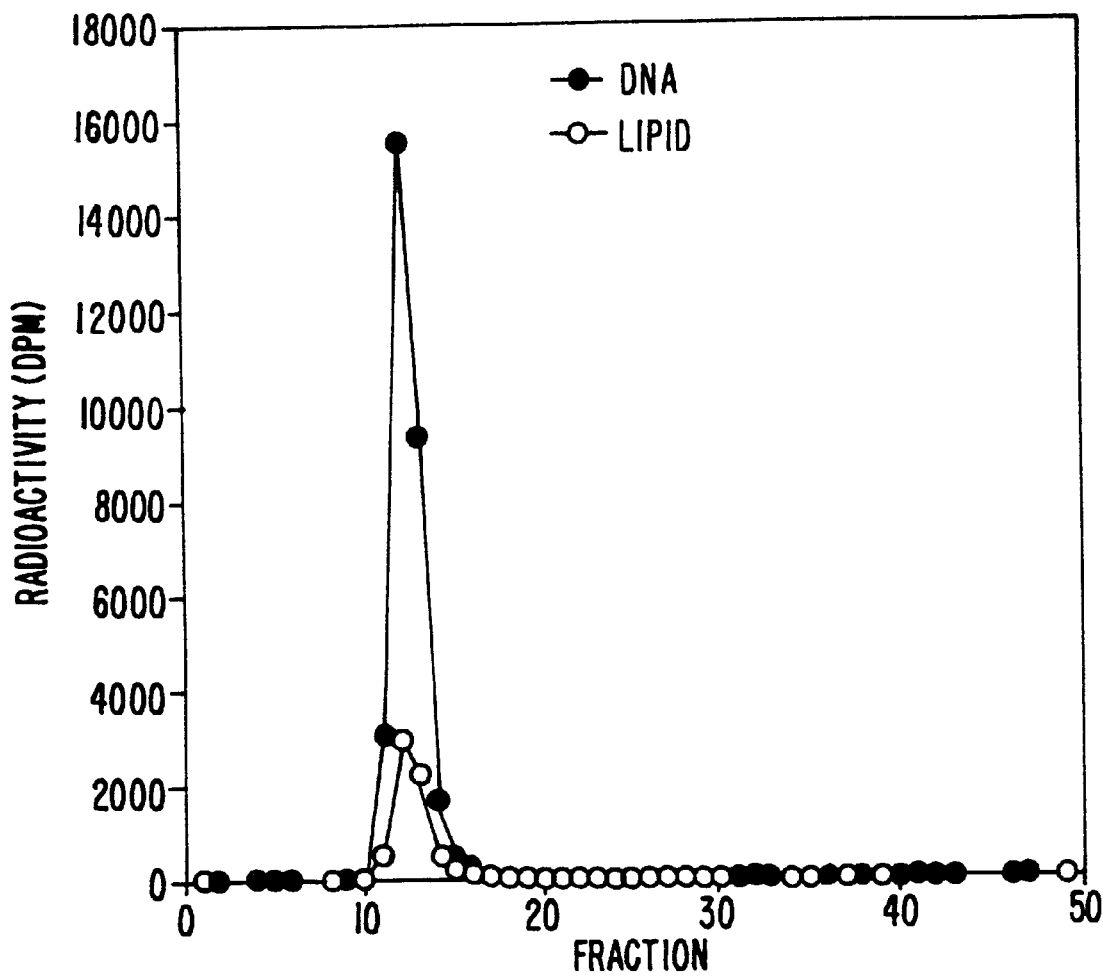
FIG. 12 shows the recovery of $^3$H-DNA and $^{14}$C-lipids from particles (prepared by reverse-phase methods) after incubation in 80% mouse serum for 15 min at 37° C. Lipid composition is POPC:DODAC:PEG-Cer($C_{20}$).

The stability of plasmid-lipid particles was assessed by incubation of a 50 μL aliquot in 500 μL of mouse serum (Cedar Lane) for 15 min at 37° C. A 500 μL aliquot of the incubation mixture was eluted in HBS on a Sepharose CL4B column (see FIG. 12). Comigration of the plasmid and lipid in the void volume strongly suggests that no plasmid degradation has occurred. Any serum associated plasmid or lipid should have been detected as a peak at around fraction 35 (see control results in FIG. 11).

Serum Stability of Plasmid-Lipid Particles Prepared by Dialysis (particles prepared from DOPE:DODAC:PEG-Cer($C_{20}$))

Figure 13:
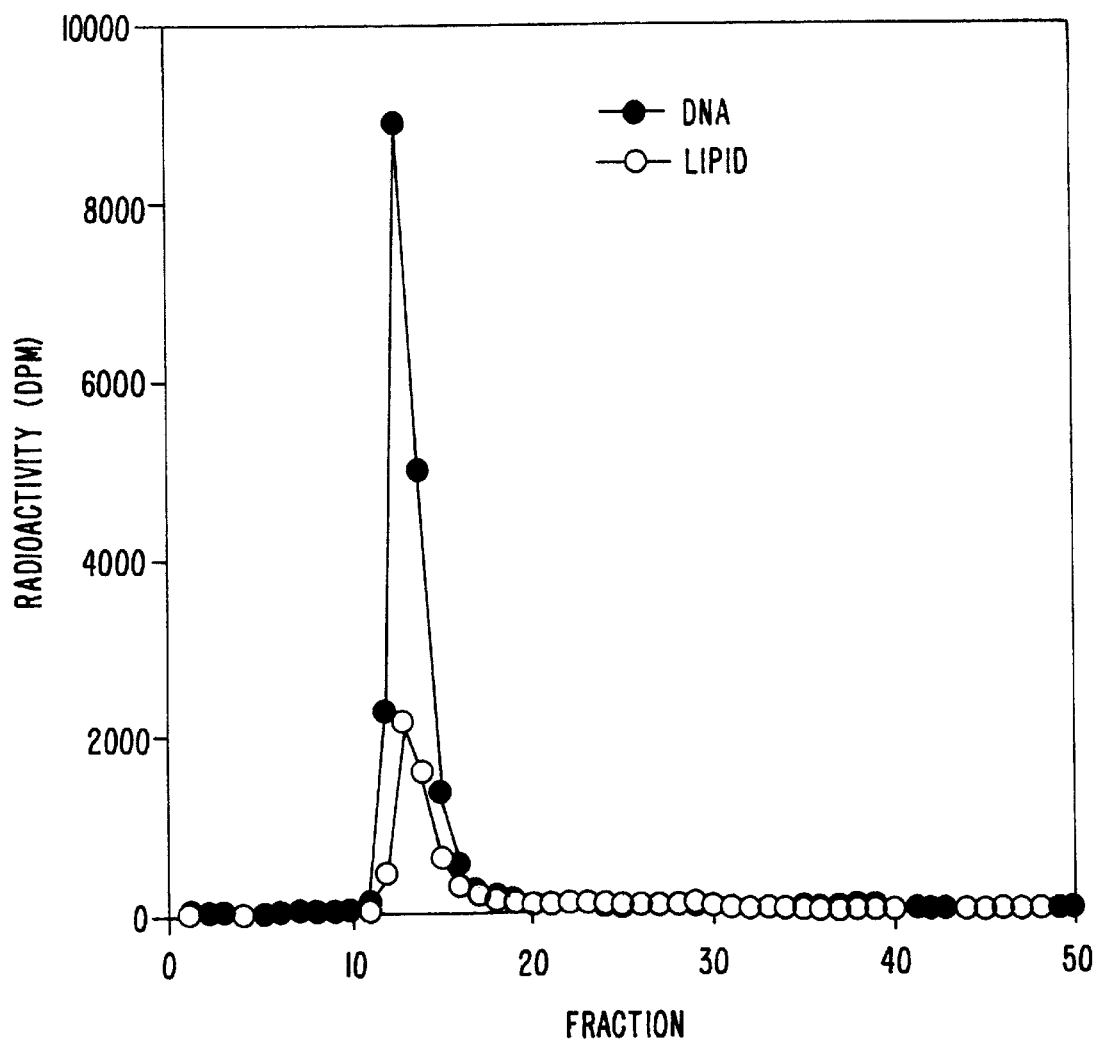
FIG. 13 shows the recovery of $^3$H-DNA and $^{14}$C-lipids from particles (prepared by detergent dialysis methods) after incubation in 80% mouse serum for 30 min at 37° C. Lipid composition is DOPE:DODAC:PEG-Cer($C_{20}$).

A 50 μL aliquot of a particle suspension prepared at a DODAC:plasmid charge ratio of 4:1 was incubated in 500 μL of mouse serum at 37° C. for 30 min and eluted on a Sepharose CL-4B column as described above. FIG. 13 shows the elution profile of the sample after incubation in serum. As can be seen in FIG. 13, 94% of the plasmid is recovered in the void volume suggesting that essentially all of the plasmid recovered from anion exchange chromatography is encapsulated.

EXAMPLE 4

This example illustrates the level of plasmid encapsulated in lipid bilayers. Empty lipid complexes containing an aqueous space are relatively low in density and have a tendency to equilibrate nearer the top of a density gradient. Free plasmid is relatively high in density and will therefore equilibrate at a position nearer the bottom of the density gradient (where the Ficoll concentration is highest; more dense). Encapsulated plasmid will equilibrate on the gradient at a position between the positions of the empty lipid complexes and free plasmid.

Reverse Phase Methods (POPC:DODAC:PEG-Cer($C_{20}$))

A 100 μL aliquot of lipid complexes prepared as above but in the absence of plasmid was added to a Ficoll 400 continuous density gradient (0–7.5%) prepared in HBS (pH 7.4). Similarly a 50 μL aliquot of the plasmid:lipid particle suspension and 0.25 μL of free $^3$H-pCMV4-CAT was added to two separate Ficoll 400 gradients. The samples were centrifuged at 100,000×g for 21 hours. $^3$H-pCMV4-CAT and $^{14}$C-lipid was assessed in 250 μL aliquots in each gradient by scintillation counting.

Figure 14:
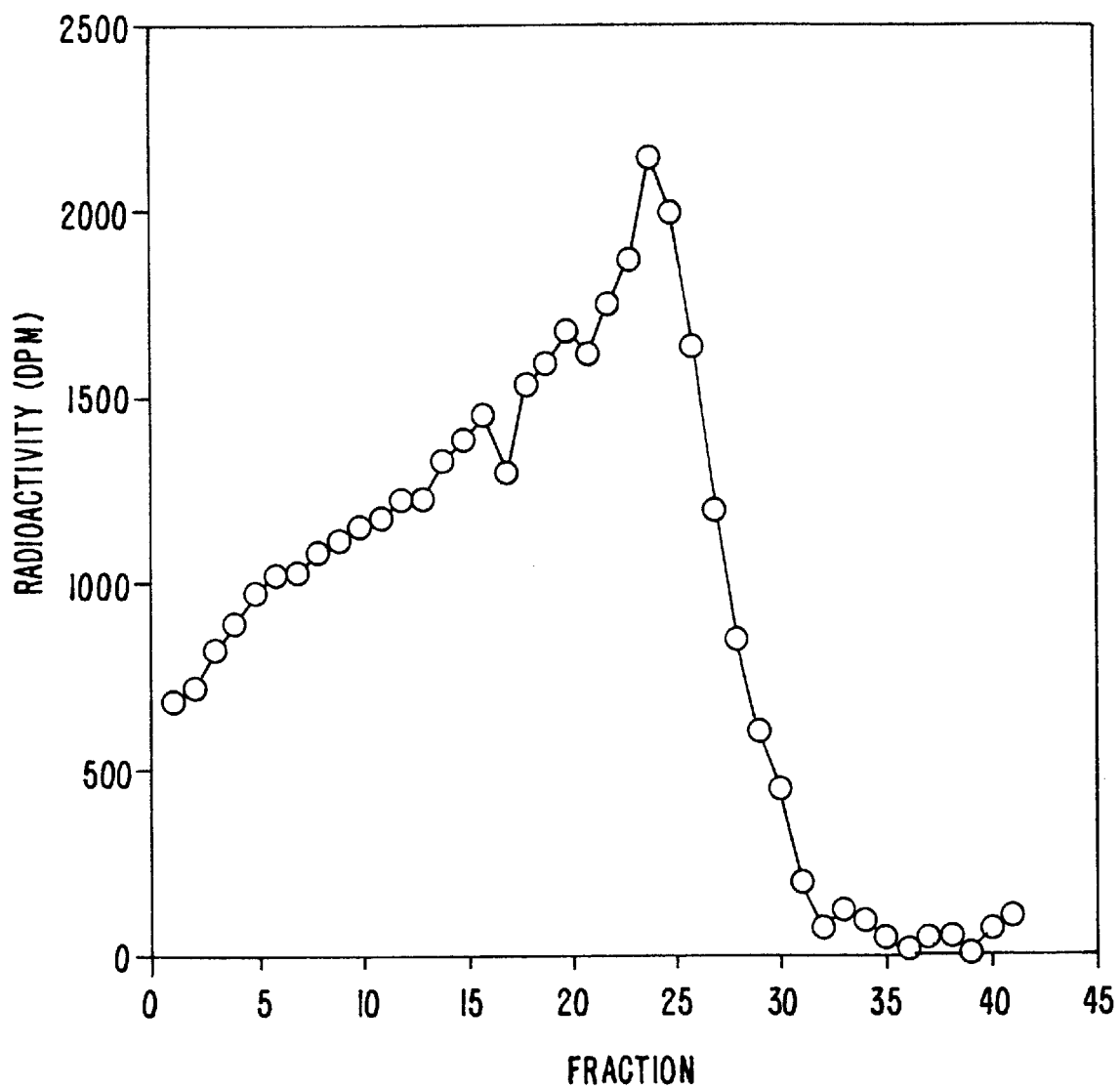
FIG. 14 provides a density gradient profile of $^{14}$C-lipid complexes prepared in the absence of DNA by reverse phase methods. Lipid composition is POPC:DODAC:PEG-Cer ($C_{20}$).
Figure 15:
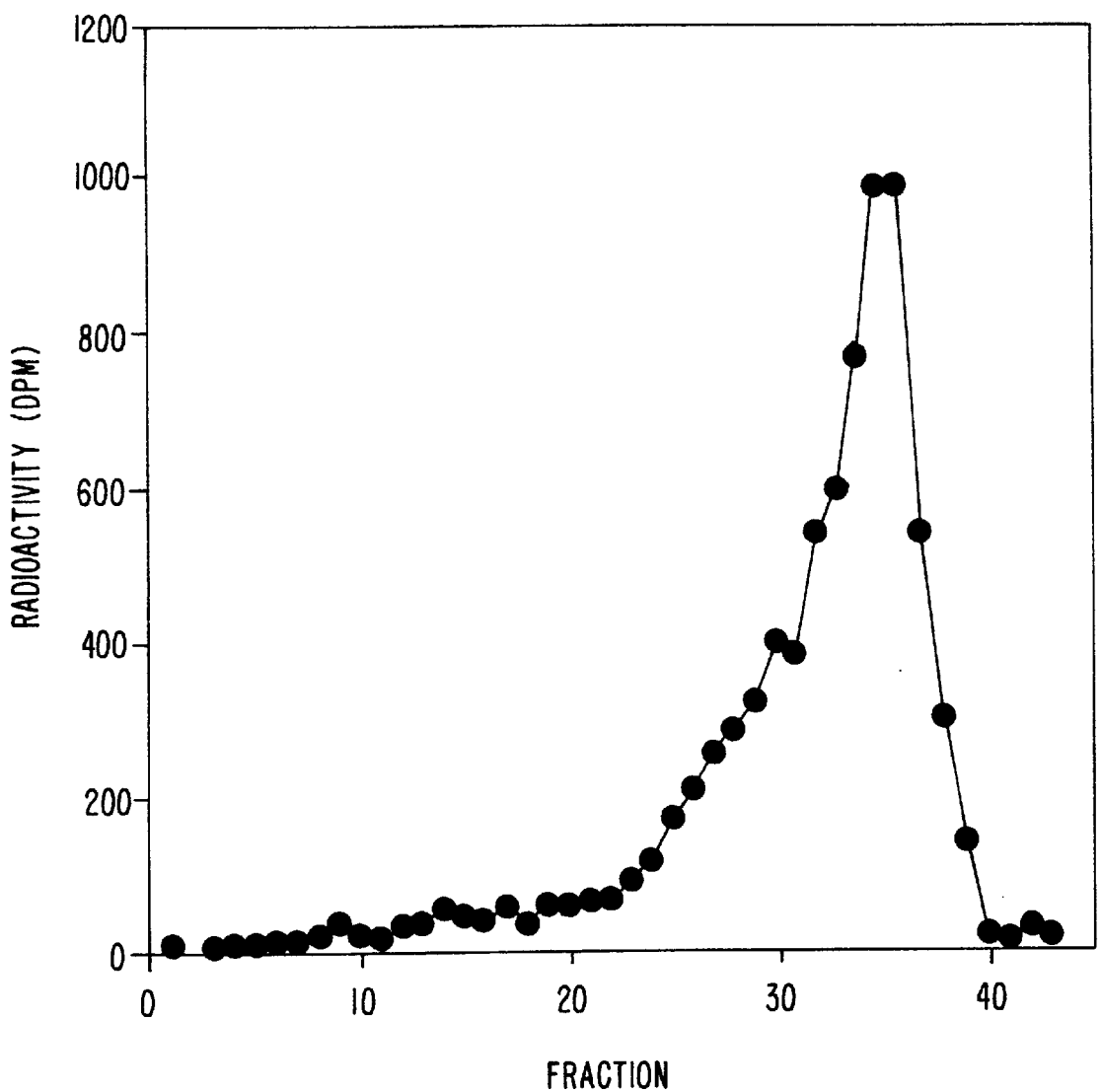
FIG. 15 provides a density gradient profile of free $^3$H-DNA (pCMV4-CAT).
Figure 16:
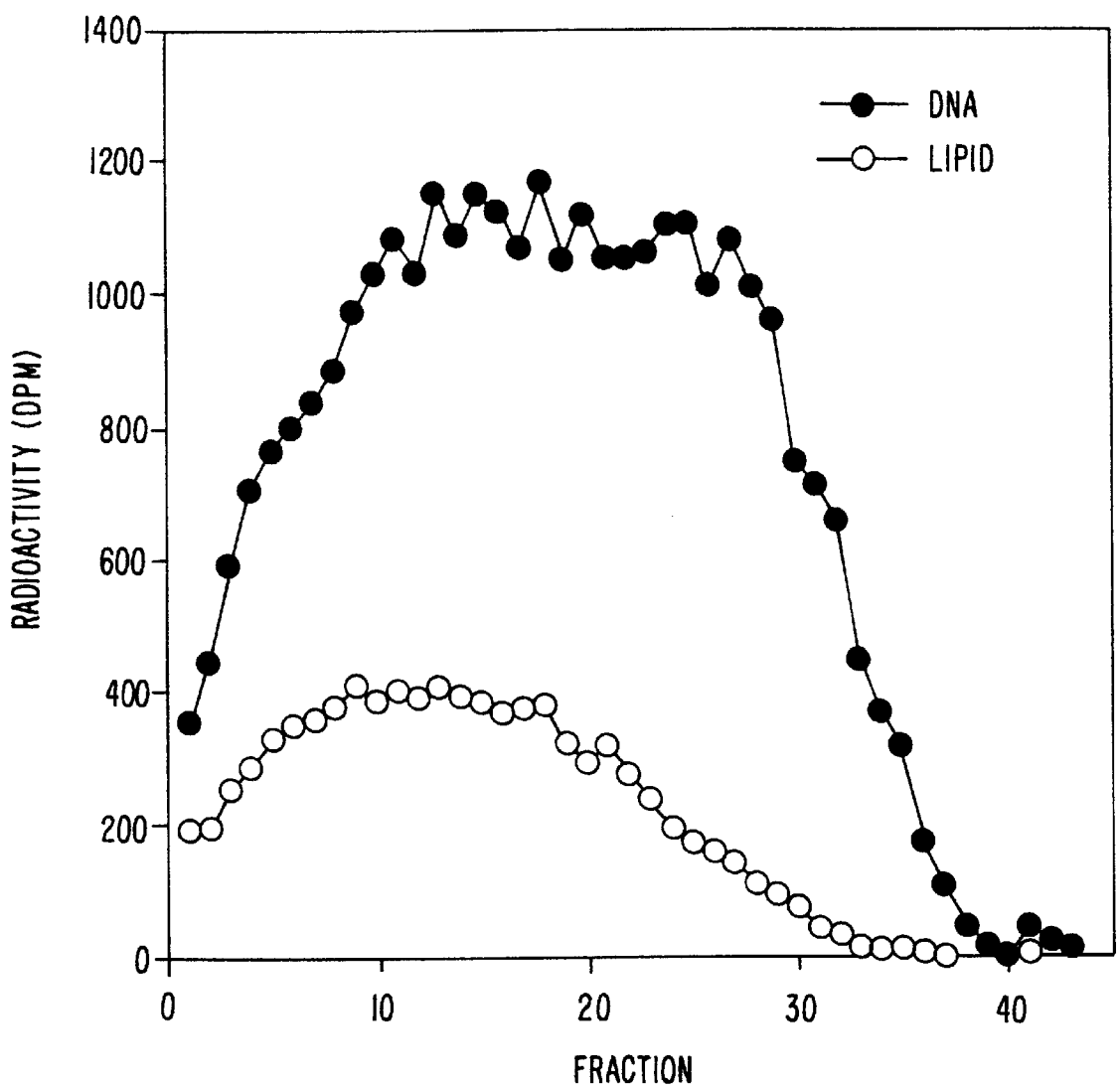
FIG. 16 provides a density gradient profile of $^3$H-DNA and $^{14}$C-lipid from particles prepared by reverse-phase methods. Lipid composition is as in FIG. 14.

The empty lipid complexes exhibited a broad range of densities peaking at approximately fraction 25 (see FIG. 14). The broad range was probably due to heterogeneity in lipid complex or liposome size and lamellarity since the complexes were only extruded three times through one 200 nm filter, rather than the usual ten times through two 100 nm filters. The free plasmid was present as a single peak near the bottom of the gradient near fraction 35 (see FIG. 15). The gradient profile of the plasmid:lipid particle suspension suggested an association of plasmid with the lipid as there was comigration of the plasmid and the lipid and the densities of both were markedly different from that of their free counterparts (see FIG. 16). The plasmid:lipid ratio was not constant over the gradient profile which can be explained by assuming that not all plasmid-lipid particles contained the same number of plasmid molecules.

Dialysis Methods (DOPE:DODAC:PEG-Cer($C_2$))

Figure 17:
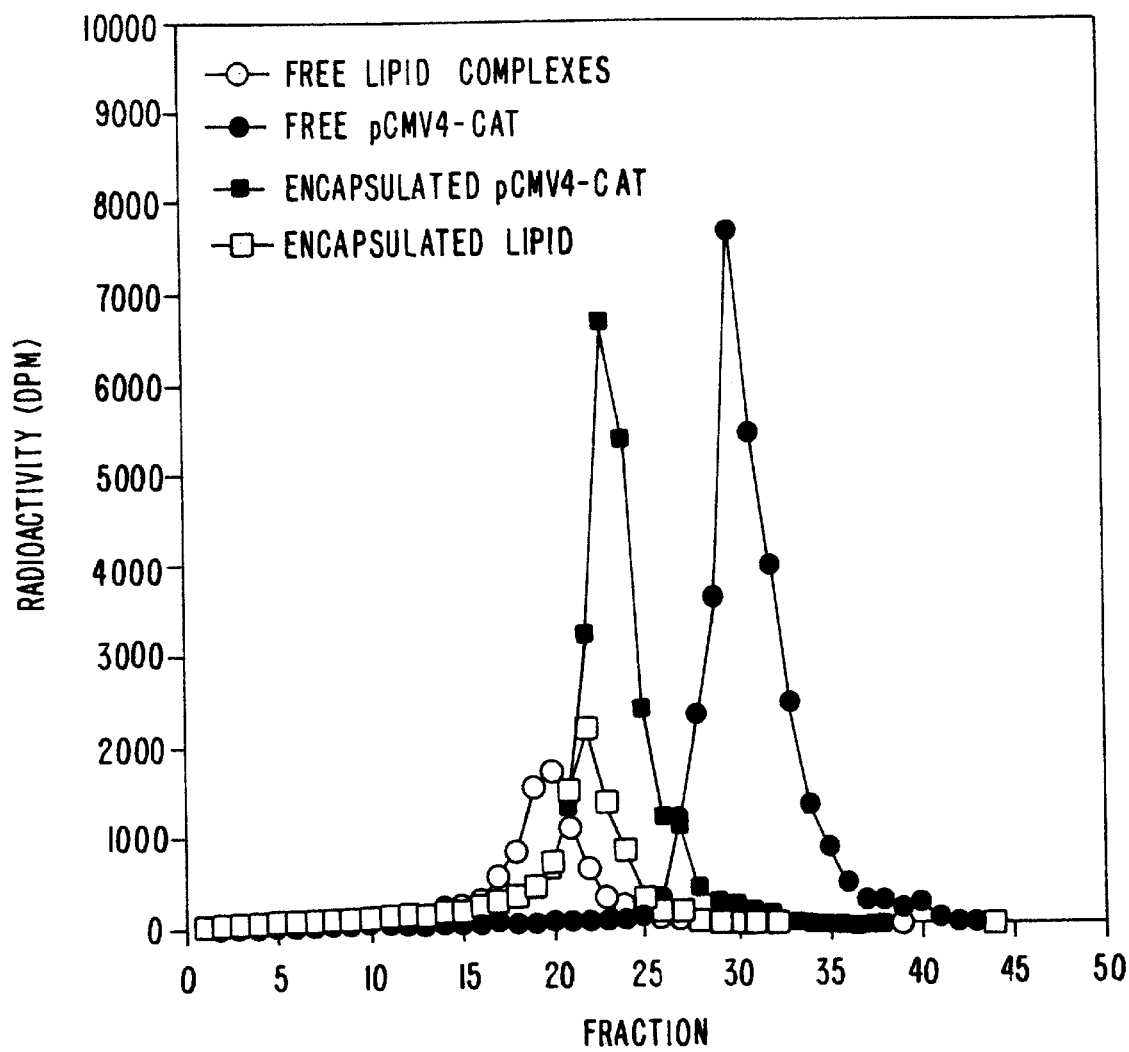
FIG. 17 provides a density gradient profile of free $^3$H-DNA, $^{14}$C-lipid complexes prepared in the absence of DNA by detergent dialysis methods and $^3$H-DNA and $^{14}$C-lipid from DNA-lipid complexes prepared by detergent dialysis. Lipid composition is DOPE:DODAC:PEG-Cer ($C_{20}$).

Plasmid-lipid particles were prepared as described in Example 1 using detergent dialysis with a lipid composition of DOPE:DODAC:PEG-Cer($C_{20}$) (83.5:6.5:10 mole %). The particles were subjected to density gradient centrifugation as described for the plasmid-lipid particles prepared by reverse phase methods. The empty lipid complexes were present as a single peak at about fraction 20 (see FIG. 17). Free plasmid was present at about fraction 31. It was evident from these controls that successful entrapment of the pCMV4-CAT was achieved as determined by the comigration of lipid and plasmid with a peak between that of the free lipid and plasmid controls.

EXAMPLE 5

This example illustrates the size distribution of plasmid-lipid particles as measured by quasielastic light scattering using a Nicomp Submicron Particle Sizer.

Figure 18:
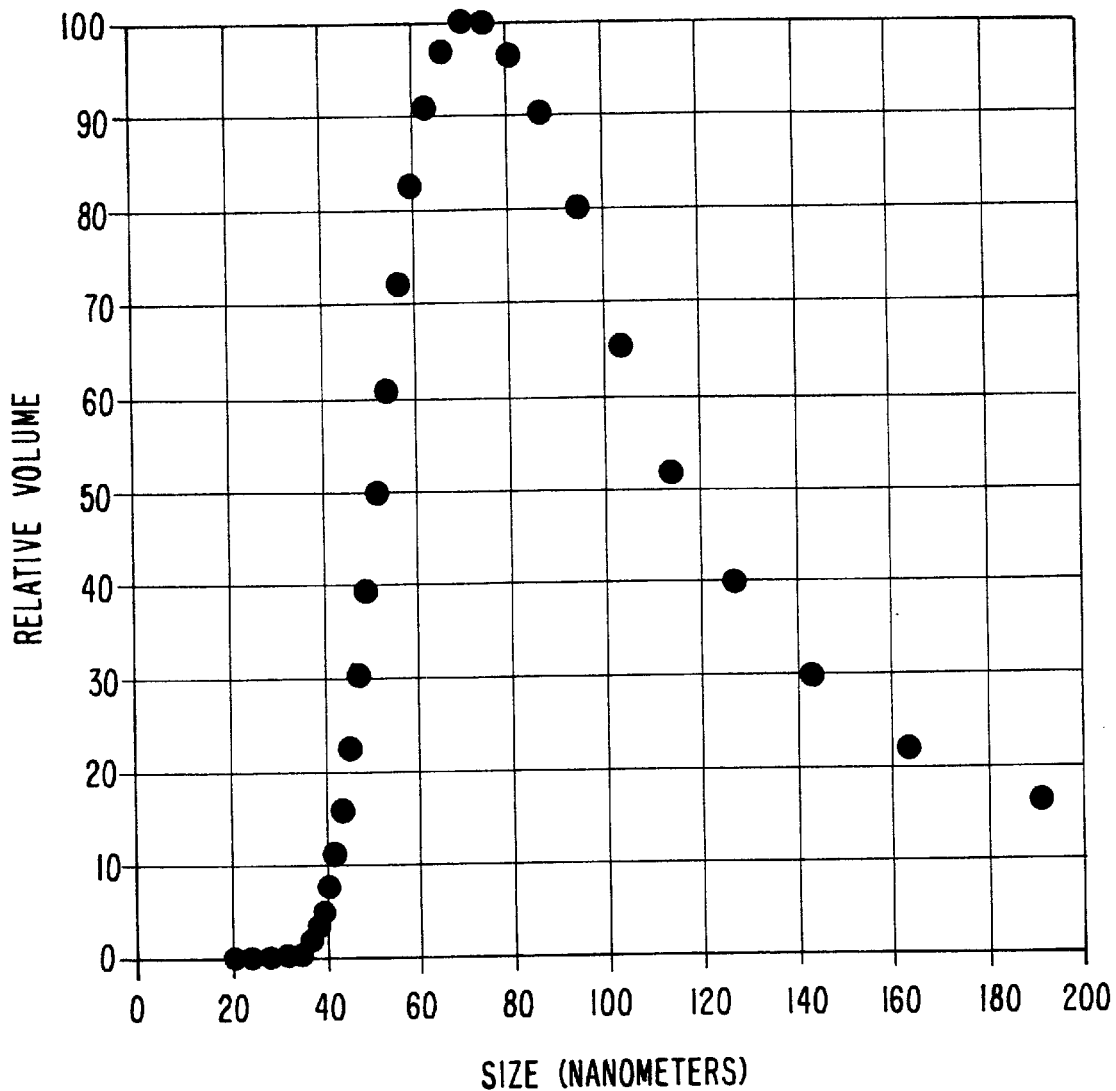
FIG. 18 provide a size distribution of DNA-lipid particles prepared by detergent dialysis methods. Lipid composition is DOPE:DODAC:PEG-Cer($C_{20}$).

Plasmid-lipid particles were prepared by detergent dialysis as described in Example 1. The lipid composition was DOPE:DODAC:PEG-Cer($C_{20}$) (83.5:6:10 mole %). The particles were sized using a Nicomp Submicron Particle Sizer (see FIG. 18). - The log normal distribution exhibited a $\chi^2$ of 0.2, indicating an extremely homogeneous distribution. The mean diameter of the particles with entrapped pCMV4-CAT plasmid was 72.4 nm.

EXAMPLE 6

This example illustrates the clearance and in vivo transfection of plasmid:lipid particles in mice.

Reverse Phase (POPC:DODAC:PEG-Cer($C_{20}$))

Figure 19:
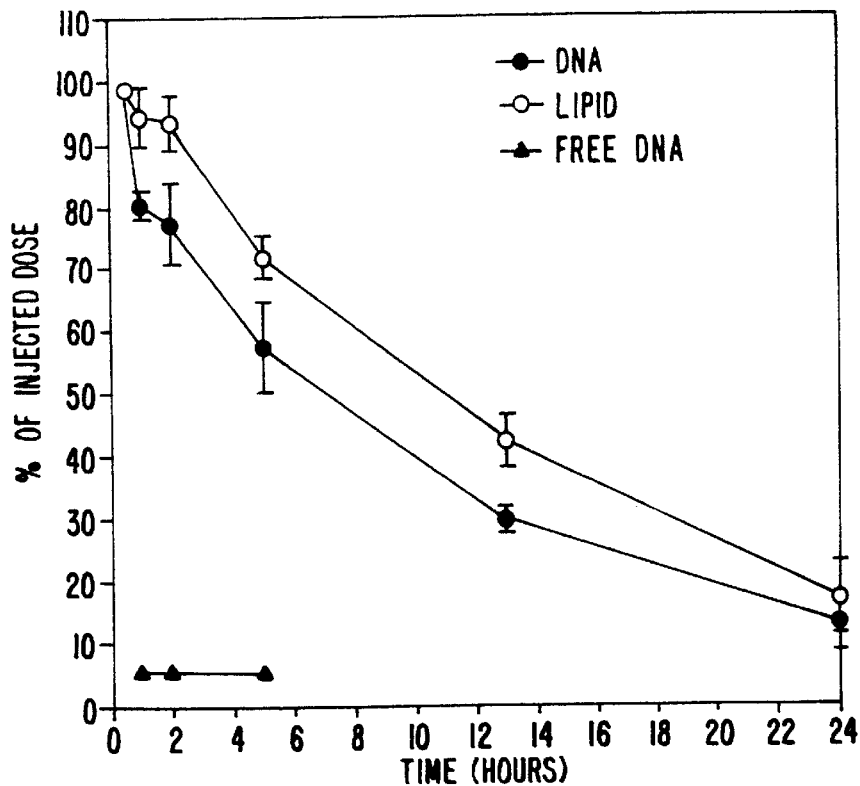
FIG. 19 shows the clearance of $^3$H-DNA and $^{14}$C-lipid from particles (prepared by reverse-phase methods) after injection into IRC mice. The figure includes free $^3$H-DNA after injection as a comparison. Lipid composition is POPC:DODAC:PEG-Cer($C_{20}$).

Encapsulated plasmid blood clearance was tested in three IRC mice as a function of percent recovered dose over time. Percent recovery of free $^3$H-plasmid was plotted over a similar time course as a control (see FIG. 19). The encapsulated plasmid exhibits a clearance rate which is much slower than that of the free $^3$H-plasmid. Additionally, the plasmid:lipid ratio does not change significantly over the time course of the experiment confirming that the plasmid clearance rate is associated with the clearance rate of the lipid carrier itself.

Detergent Dialysis (DOPE:DODAC:PEG-Cer($C_{14}$ or $C_{20}$))

Fusogenic particles of pCMV4-CAT encapsulated in DOPE:DODAC:PEG-Cer($C_{14}$ or $C_{20}$) (83.5:6.5:10 mole %) were prepared as follows:

pCMV4-CAT (50 μg)(42 μL of $^3$H-pCMV4-CAT; 108 dpm/μL, 1.19 mg/mL) was incubated with DODAC (407 μg; ~4:1 DODAC:DNA charge ratio) in 100 μL of 1 M OGP and 400 μL of water for 30 min at room temperature. This DNA:DODAC complex mixture was added to a suspension of 10 mg of DOPE:PEG-Cer($C_{14}$ or $C_{20}$) (63.5:10 mole %) and the particles were constructed as described in Example 1 (detergent dialysis). The plasmid-lipid particles for blood clearance studies contained 0.75 μL of $^{14}$C-cholesteryl hexadecyl ether (CHE) (6.66 μL/μCi) in 100 μL of 1 M OGP and 400 μL of water. Control particles prepared without DNA contained 2 μL of $^{14}$C-CHE for the particles containing PEG-Cer($C_{14}$) and 0.75 μL of $^{14}$C-CHE for the particles containing PEG-Cer($C_{20}$). For in vivo transfection, no $^{14}$C-lipid label was used as it would interfere with the CAT assay.

Clearance of pCMV4CAT "DNA" Encapsulated in DOPE:DODAC:PEG-Cer ($C_{14}$ and $C_{20}$)

External "untrapped" DNA was removed by anion exchange chromatography using DEAE Sepharose CL-6B prior to injection into mice. Encapsulation efficiencies were approximately 42% for the systems containing PEG-Cer ($C_{20}$) and 60% for the systems containing PEG-Cer($C_{14}$).

Three groups of three female ICR mice (20–25 g) were injected with 200 μL of DNA-encapsulated DOPE:DODAC:PEG-Cer($C_{20}$) ((83.5:6.5:10 mole %) each and another set of nine mice were injected with 200 μL of DNA-encapsulated DOPE:DODAC:PEG-Cer($C_{14}$) ((83.5:6.5:10 mole %) each. One group of mice was sacrificed and blood was taken at each of three time points (1, 2 and 5 hours). The plasma was separated from whole blood by centrifugation in 0.5 mL EDTA coated Tainer tubes. A 200 μL aliquot of the plasma from each mouse was assayed for $^3$H-DNA and $^{14}$C-lipid by scintillation counting.

Control particles (no DNA) which had been passed down an anion exchange column also were also analyzed. Two hundred microliters each of DOPE:DODAC:PEG-Cer($C_{20}$) control particles was injected into one group of three female ICR mice and 200 µL of DOPE:DODAC:PEG-Cer($C_{14}$) control particles was injected into three groups of three of the ICR mice. The plasma was analyzed for $^{14}$C-lipid after 1, 2 and 5 hours.

Figure 20:
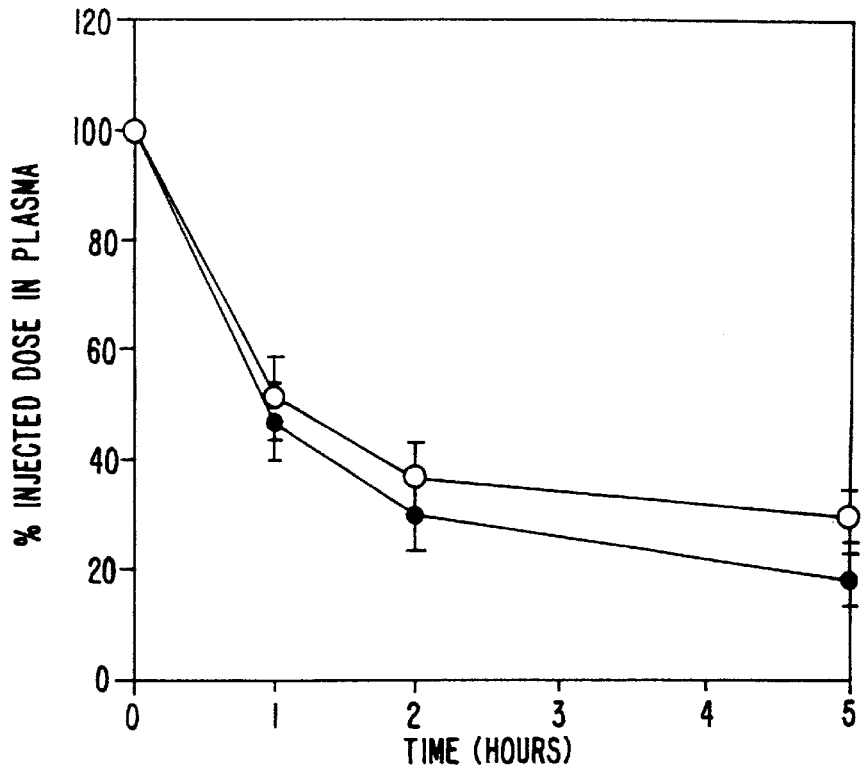
FIG. 20 shows the clearance of $^3$H-DNA and $^{14}$C-lipid from particles (prepared by detergent dialysis methods) after injection into IRC mice. Lipid composition is DOPE:DODAC:PEG-Cer($C_{20}$) (83.5:6.5:10 mole %).

FIG. 20 shows the clearance of DNA encapsulated in particles composed of DOPE:DODAC:PEG-Cer($C_{20}$) ((83.5:6.5:10 mole %). The DNA and lipid are cleared much less rapidly from the circulation than when PEG-Cer($C_{14}$) is used (see FIG. 21). Nearly 50% of the lipid and DNA are present after 1 hour. A significant amount of DNA and lipid were still present after 5 hr. The amount of DNA and lipid injected was 1.8 µg and 853 µg, respectively. Control particles exhibited a clearance similar to that of the plasmid-lipid particles.

Figure 21:
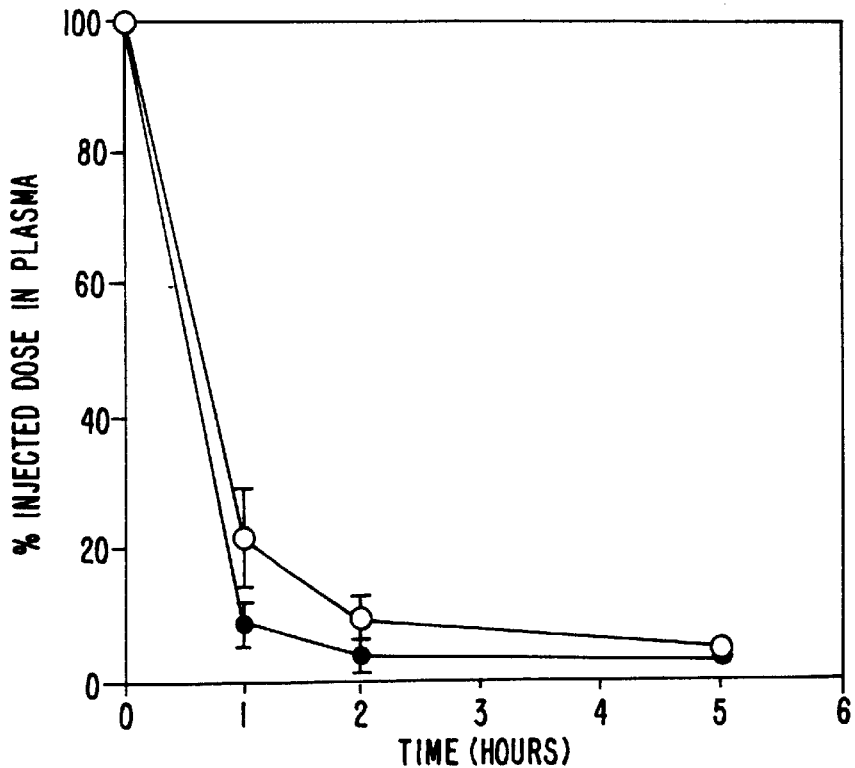
FIG. 21 shows the clearance of $^3$H-DNA and $^{14}$C-lipid from particles (prepared by detergent dialysis methods) after injection into IRC mice. Lipid composition is as in FIG. 20 except that PEG-Cer($C_{20}$) is replaced with PEG-Cer($C_{14}$).

FIG. 21 shows the clearance of DNA encapsulated in particles composed of DOPE:DODAC:PEG-Cer($C_{14}$) ((83.5:6.5:10 mole %). Both DNA and lipid are 5 cleared rapidly from the circulation with only about 20% of the lipid and 10% of the DNA present in the plasma after 1 hr. The amount of DNA and lipid injected was 2.7 µg and 912 µg, respectively. Control particles exhibited a clearance similar to that of the plasmid-lipid particles.

In Vivo Transfection in Lung, Liver and Spleen

Three groups of four IRC mice were injected via tail vein with pCMV4-CAT encapsulated in lipid particles composed of DOPE:DODAC:PEG-Cer($C_{14}$) (83.5:6.5:10 mole %, "A") or DOPE:DODAC:PEG-Cer($C_{20}$) (83.5:6.5:10 mole %, "B"), prepared as described above. The mice were sacrificed after 2, 4 and 8 days and the lung, liver and spleen were assayed for CAT activity according to a modification of Deigh, *Anal. Biochem.* 156:251–256 (1986). The amount of plasmid injected was 2.6 µg for the particles containing PEG-Cer($C_{14}$) and 1.5 µg for the particles containing PEG-Cer($C_{20}$).

Figure 22:
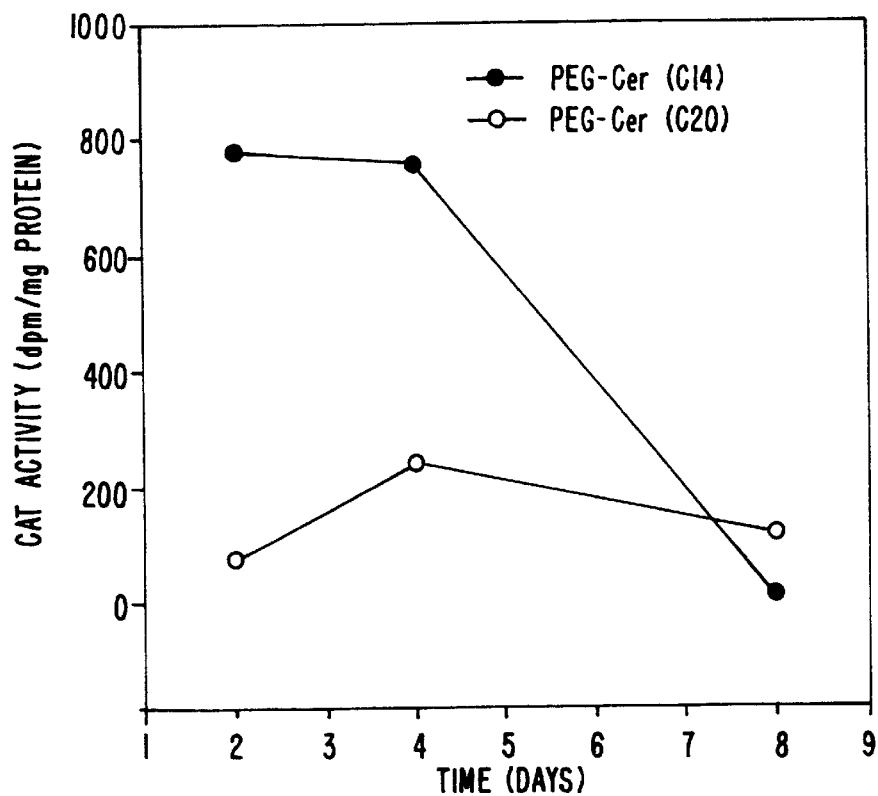
FIG. 22 shows the results of in vivo transfection which occurs in the lungs of mice. Lipid composition is DOPE:DODAC:PEG-Cer($C_{20}$ or $C_{14}$) (83.5:6.5:10 mole %).

FIG. 22 shows the results of in vivo transfection achieved in the lung. As can be seen from this figure, treatment with formulation "A" provided excellent transfection efficiency (based on CAT activity) up to 4 days. Formulation "B", while resulting in overall lower levels of CAT activity, provided relatively constant levels of enzyme activity over 8 days.

Figure 23:
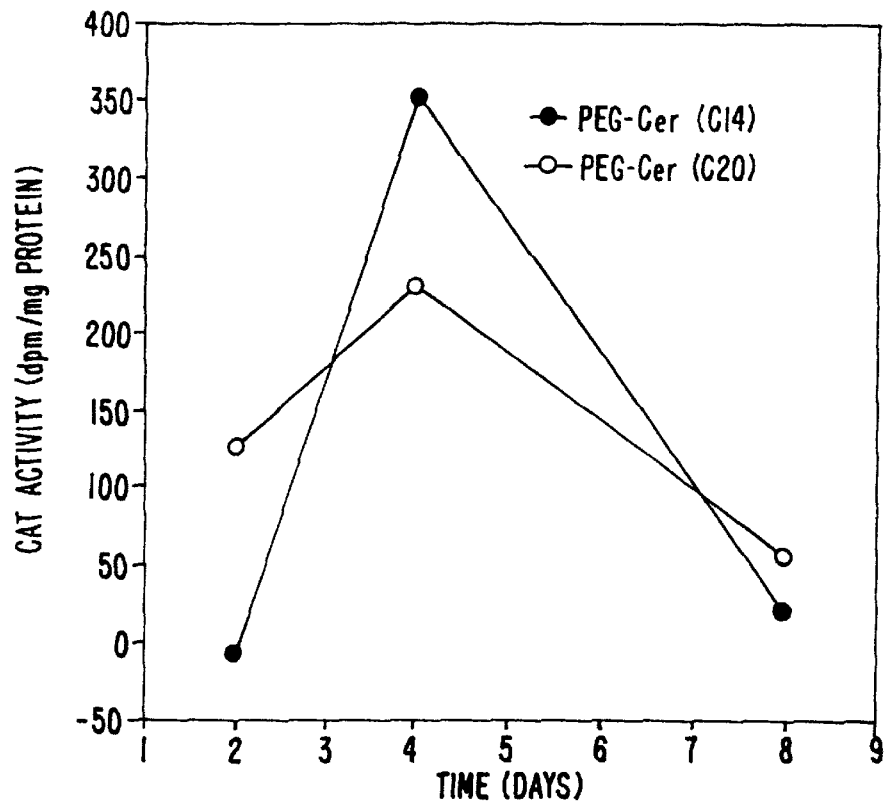
FIG. 23 shows the results of in vivo transfection which occurs in the liver of mice. Lipid composition is as in FIG. 22.

FIG. 23 shows the results of transfection achieved in the liver. For both formulations, transfection (and CAT activity) reached a maximum at 4 days.

Figure 24:
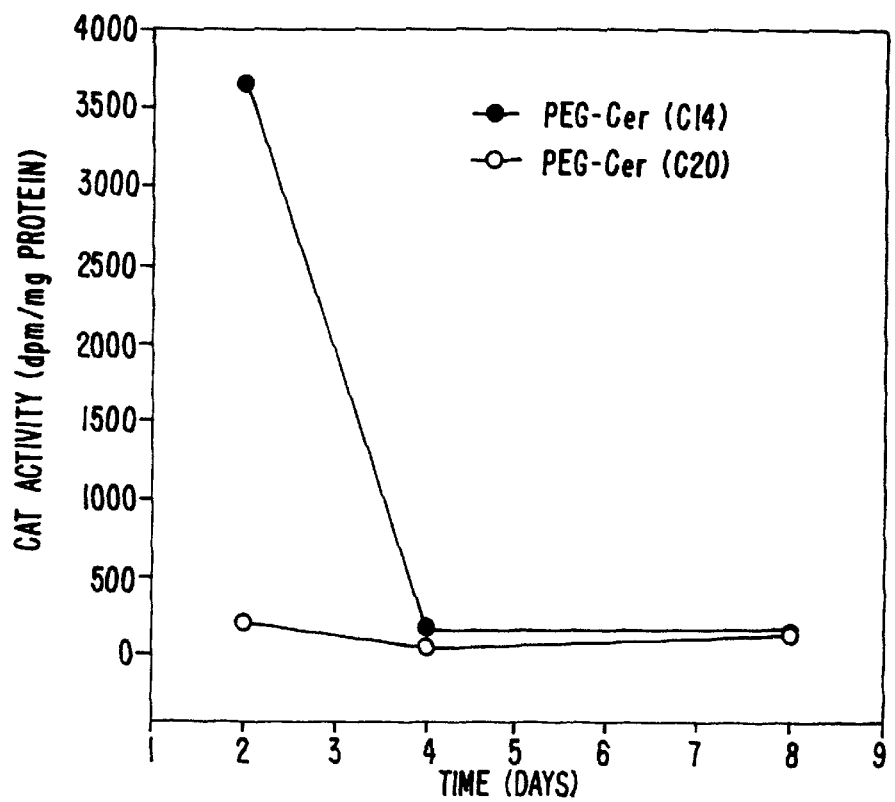
FIG. 24 shows the results of in vivo transfection which occurs in the spleen of mice. Lipid composition is as in FIG. 22.

FIG. 24 shows the results of transfection achieved in the spleen wherein the maximum transfection was found for both formulations to occur after 2 days.

VII. Conclusion

As discussed above, in accordance with one of its aspects, the present invention provides methods for preparing serum-stable plasmid-lipid particles which are useful for the transfection of cells, both in vitro and in vivo.

All publications, patents and patent applications mentioned in this specification are herein incorporated by reference into the specification to the same extent as if each individual publication, patent or patent application was specifically and individually indicated to be incorporated herein by reference.

Although the foregoing invention has been described in some detail by way of illustration and example for purposes of clarity of understanding, it will be obvious that certain changes and modifications may be practiced within the scope of the appended claims.

What is claimed is:

1. A method for the preparation of serum-stable plasmid-lipid particles, comprising:
    (a) combining a plasmid with cationic lipids in a detergent solution to provide a coated plasmid-lipid complex;
    (b) contacting non-cationic lipids with said coated plasmid-lipid complex to provide a solution comprising detergent, a plasmid-lipid complex and non-cationic lipids; and
    (c) removing said detergent from said solution of step (b) to provide a solution of serum-stable plasmid-lipid particles, wherein said plasmid is encapsulated in a lipid bilayer and said particles are resistant to degradation in serum, and wherein the particles have a diameter ranging from about 50 to about 150 nm.

2. A method in accordance with claim 1, wherein said removing is by dialysis.

3. A method in accordance with claim 1, wherein step (b) further comprises adding a polyethylene glycol-lipid conjugate.

4. A method in accordance with claim 3, wherein said polyethylene glycol-lipid conjugate is a PEG-ceramide conjugate.

5. A method in accordance with claim 1, further comprising;
    (d) sizing said particles to achieve a uniform particle size.

6. A method in accordance with claim 1, wherein said cationic lipids are selected from the group consisting of DODAC, DDAB, DOTAP, DOTMA, DOSPA, DOGS, DC-Chol and combinations thereof.

7. A method in accordance with claim 1, wherein said non-cationic lipids are selected from the group consisting of DOPE, POPC, EPC and combinations thereof.

8. A method in accordance with claim 1, wherein said detergent solution comprises a detergent having a critical micelle concentration of between about 20 mM and 50 mM.

9. A method in accordance with claim 8, wherein said detergent is n-octyl-β-D-glucopyranoside.

10. A method for introducing a plasmid into a cell, comprising:
    (a) preparing a plasmid-lipid particle according to the method of claim 1; and
    (b) contacting said cell with said plasmid-lipid particle for a period of time sufficient to introduce said plasmid into said cell.

11. A method in accordance with claim 10, wherein said plasmid-lipid particle comprises a plasmid, DODAC, POPC and a PEG-Ceramide selected from the group consisting of PEG-Cer-$C_{20}$ and PEG-Cer-$C_{14}$.

12. A method in accordance with claim 10, wherein said plasmid-lipid particle comprises a plasmid, DODAC, DOPE and a PEG-Ceramide selected from the group consisting of PEG-Cer-$C_{20}$ and PEG-Cer-$C_{14}$.

13. In a method of gene therapy involving the introduction of a plasmid via a plasmid-lipid composition into a cell resulting in sufficient expression to effect a phenotypic change, the improvement which comprises
    (a) preparing a plasmid-lipid particle according to the method of claim 1; and
    (b) contacting said cell with said plasmid-lipid particle for a period of time sufficient to introduce said plasmid into said cell.

14. A method for the preparation of serum-stable plasmid-lipid particles, comprising:
    (a) preparing a mixture comprising cationic lipids and non-cationic lipids in an organic solvent;

(b) contacting an aqueous solution of plasmid with said mixture prepared in step (a) to provide a single phase; and (c) removing said organic solvent to provide a suspension of plasmid-lipid particles, wherein said plasmid is encapsulated in a lipid layer and said particles are resistant to degradation in serum, and wherein the particles have a diameter ranging from about 50 to about 150 nm.

15. A method in accordance with claim 10, wherein said non-cationic lipids comprise a polyethylene glycol-lipid conjugate.

16. A method in accordance with claim 15, wherein said polyethylene glycol-lipid conjugate is a PEG-ceramide conjugate.

17. A method in accordance with claim 14 further comprising;

(d) sizing said plasmid-lipid particles to achieve a uniform particle size.

18. A method in accordance with claim 10, wherein said cationic lipids are selected from the group consisting of DODAC, DDAB, DOTAP, DOTMA, DOSPA, DOGS, DC-Chol and combinations thereof.

19. A method in accordance with claim 14, wherein said non-cationic lipids are selected from the group consisting of DOPE, POPC, EPC and combinations thereof.

20. A method for introducing a plasmid into a cell, comprising:

(a) preparing a plasmid-lipid particle according to the method of claim 14; and (b) contacting said cell with said plasmid-lipid particle for a period of time sufficient to introduce said plasmid into said cell.

21. A method in accordance with claim 20, wherein said plasmid-lipid particle comprises a plasmid, DODAC, POPC and a PEG-Ceramide selected from the group consisting of PEG-Cer-$C_{20}$ and PEG-Cer-$C_{14}$.

22. A method in accordance with claim 20, wherein said plasmid-lipid particle comprises a plasmid, DODAC, DOPE and a PEG-Ceramide selected from the group consisting of PEG-Cer-$C_{20}$ and PEG-Cer-$C_{14}$.

23. In a method of gene therapy involving the introduction of a plasmid via a plasmid-lipid composition into a cell resulting in sufficient expression to effect a phenotypic change, the improvement which comprises (a) preparing a plasmid-lipid particle according to the method of claim 14; and (b) contacting said cell with said plasmid-lipid particle for a period of time sufficient to introduce said plasmid into said cell.

24. A method for the preparation of serum-stable plasmid-lipid particles, comprising:

a) combining a plasmid with cationic lipids in a first detergent solution to provide a coated plasmid-lipid complex;

b) contacting non-cationic lipids with said coated plasmid-lipid complex to provide a second solution comprising detergent, a plasmid-lipid complex and non-cationic lipids and adding a polyethylene glycol-lipid conjugate to said second solution; and c) removing said detergent from said second solution to provide a solution of serum-stable plasmid-lipid particles, wherein said plasmid is encapsulated in a lipid bilayer and said particles are resistant to degradation in serum, and wherein the particles have a diameter ranging from about 50 to about 150 nm.

25. A method for the preparation of serum-stable plasmid-lipid particles, comprising:

a) preparing a mixture comprising cationic lipids and non-cationic lipids in an organic solvent, wherein said non-cationic lipids comprise a polyethylene glycol-lipid conjugate;

b) contacting an aqueous solution of plasmid with said mixture prepared in step (a) to provide a single phase; and c) removing said organic solvent to provide a suspension of plasmid-lipid particles, wherein said plasmid is encapsulated in a lipid bilayer and said particles are resistant to degradation in serum, and wherein the particles have a diameter ranging from about 50 to about 150 nm.

26. A method in accordance with claim 25, wherein said polyethylene glycol-lipid conjugate is a PEG-ceramide conjugate.

27. A method for introducing a plasmid into a cell, comprising:

(a) preparing a plasmid-lipid particle according to the method of claim 25; and (b) contacting said cell with said plasmid-lipid particle for a period of time sufficient to introduce said plasmid into said cell.

28. A method in accordance with claim 27, wherein said plasmid-lipid particle comprises a plasmid, DODAC, POPC and a PEG-Ceramide selected from the group consisting of PEG-Cer-$C_{20}$ and PEG-Cer-$_{14}$.

29. A method in accordance with claim 27, wherein said plasmid-lipid particle comprises a plasmid, DODAC, DOPE and a PEG-Ceramide selected from the group consisting of PEG-Cer-$C_{20}$ and PEG-Cer-$C_{14}$.

* * * * *